US012122036B2

(12) United States Patent
Sitzmann et al.

(10) Patent No.: US 12,122,036 B2
(45) Date of Patent: *Oct. 22, 2024

(54) BODY SUPPORT DEVICE

(71) Applicant: SITZMANN TOOLS, LLC, Seattle, WA (US)

(72) Inventors: Beau Sitzmann, Seattle, WA (US); Tom Swetish, Bellingham, WA (US)

(73) Assignee: Evolutionary Tools, Inc., Seattle, WA (US)

( * ) Notice: Subject to any disclaimer, the term of this patent is extended or adjusted under 35 U.S.C. 154(b) by 35 days.

This patent is subject to a terminal disclaimer.

(21) Appl. No.: 17/890,893

(22) Filed: Aug. 18, 2022

(65) Prior Publication Data

US 2023/0082284 A1    Mar. 16, 2023

Related U.S. Application Data

(63) Continuation of application No. 16/738,952, filed on Jan. 9, 2020, now Pat. No. 11,458,612.

(60) Provisional application No. 62/790,325, filed on Jan. 9, 2019.

(51) Int. Cl.
| | |
|---|---|
| B25H 5/00 | (2006.01) |
| A61F 5/02 | (2006.01) |
| A61F 5/03 | (2006.01) |

(52) U.S. Cl.
CPC ............ B25H 5/00 (2013.01); A61F 5/028 (2013.01); A61F 5/03 (2013.01)

(58) Field of Classification Search
CPC ... B25H 5/00; A61F 5/028; A61F 5/03; A61F 5/026; A61F 2007/0018; A61F 2/32; A61F 2005/0183; A61F 2007/004; A61F 2013/49049; A61F 2013/00493; A61F 5/3784; A61F 5/02; A47C 16/00; F16M 13/00

See application file for complete search history.

(56) References Cited

U.S. PATENT DOCUMENTS

| | | | |
|---|---|---|---|
| 1,417,250 | A | 5/1922 | Kelly |
| 2,288,013 | A | 6/1942 | Moynahan et al. |
| 4,058,119 | A | 11/1977 | Rosequist |
| 4,637,536 | A | 1/1987 | Wong |

(Continued)

OTHER PUBLICATIONS

International Search Report and Written Opinion mailed Feb. 4, 2016, issued in corresponding International Application No. PCT/US2015/62313, filed Nov. 24, 2015, 9 pages.

(Continued)

*Primary Examiner* — Tarla R Patel
(74) *Attorney, Agent, or Firm* — Polsinelli PC

(57) ABSTRACT

A body support device includes a body attachment portion having a first side and a second side, the first side including a plurality of receiving channels, and a leg assembly including an elongate member having an elongate body, a first end having a coupling interface configured for releasable attachment with the body attachment portion and a second end extending from the body attachment portion, wherein the coupling interface includes a hinge assembly having a first hinging portion and a second hinging portion, and wherein the second hinging portion is configured for pivotal movement such that the elongate member is configured for movement between extended and retracted positions.

20 Claims, 17 Drawing Sheets

(56) References Cited

U.S. PATENT DOCUMENTS

| | | | |
|---|---|---|---|
| 4,964,553 | A | 10/1990 | Glynn |
| 5,326,122 | A | 7/1994 | Duffy |
| 5,876,361 | A | 3/1999 | Harris |
| 6,799,592 | B1 | 10/2004 | Reynolds |
| 7,303,537 | B1 | 12/2007 | Snyder et al. |
| 7,325,868 | B2 | 2/2008 | West et al. |
| 7,624,737 | B2 * | 12/2009 | Klemm ................. A47C 16/00 5/624 |
| 7,980,625 | B2 | 7/2011 | Worthington |
| D699,932 | S | 2/2014 | Lubart |
| 9,557,002 | B2 * | 1/2017 | Wong ................. F16M 11/2064 |
| 11,458,612 | B2 * | 10/2022 | Sitzmann ................. B25H 5/00 |
| 2001/0047904 | A1 | 12/2001 | Antonio |
| 2002/0100846 | A1 | 8/2002 | Tinsley |
| 2003/0034037 | A1 | 2/2003 | Klemm |
| 2009/0309001 | A1 * | 12/2009 | Worthington .......... A47C 16/00 248/354.5 |
| 2012/0311757 | A1 | 12/2012 | Miller |
| 2013/0067642 | A1 | 3/2013 | Chen |
| 2013/0306807 | A1 * | 11/2013 | Liang .................... F16M 11/38 248/124.1 |

OTHER PUBLICATIONS

International Preliminary Report on Patentability and Written Opinion mailed May 30, 2017, issued in corresponding International Application No. PCT/US2015/62313, filed Nov. 24, 2015, 7 pages.

* cited by examiner

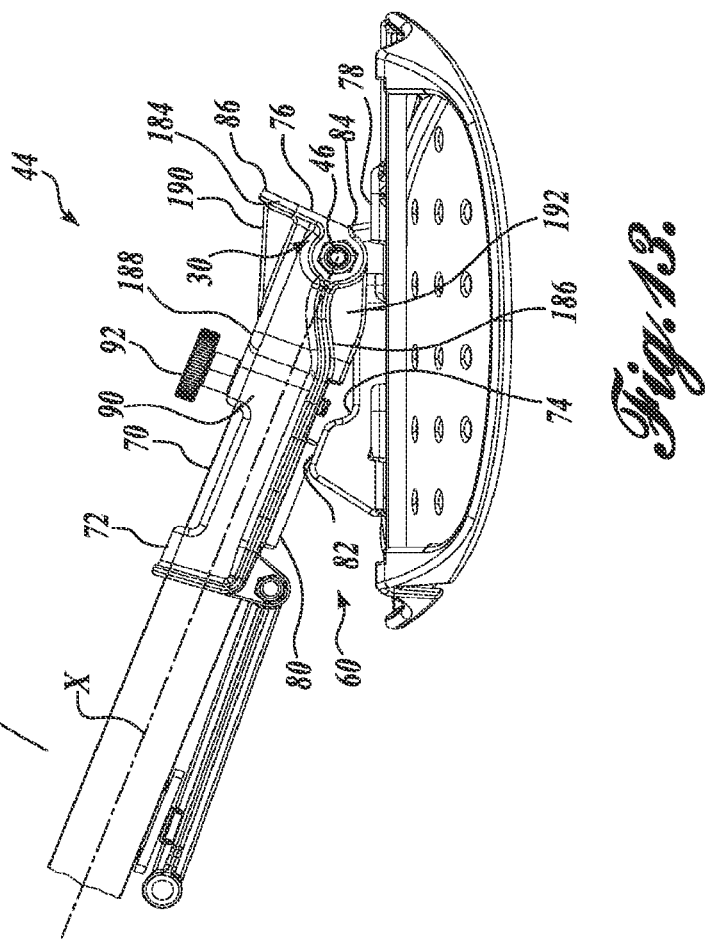
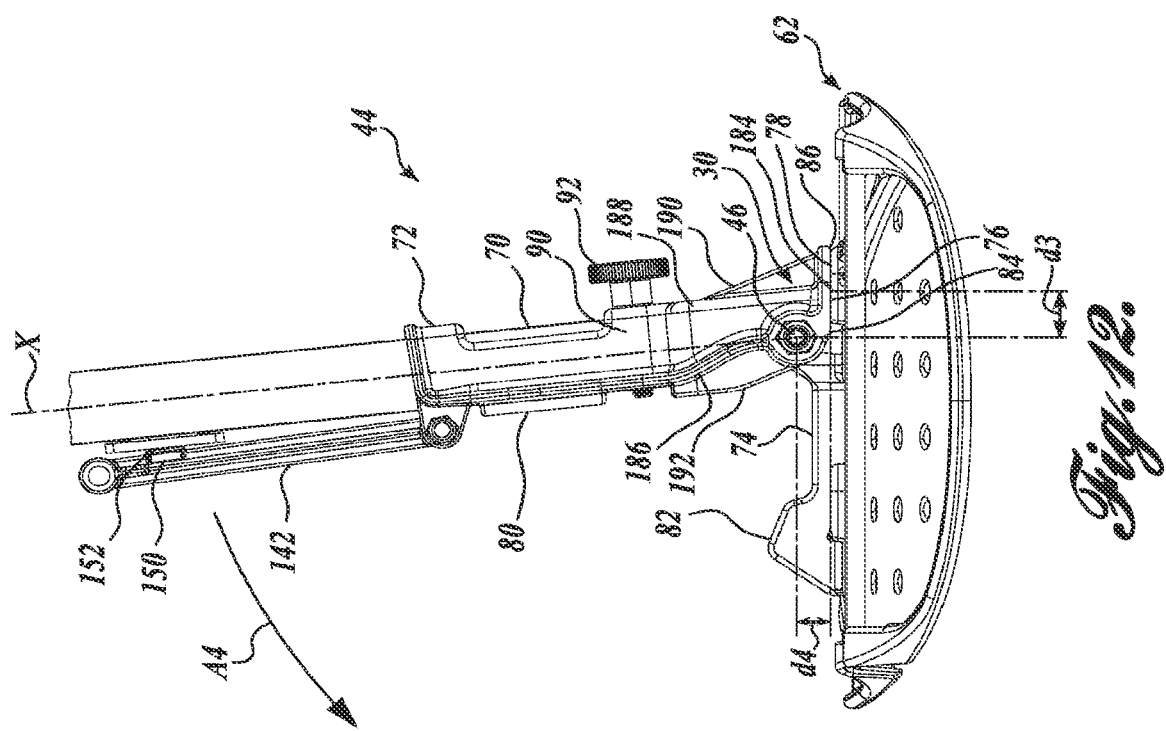

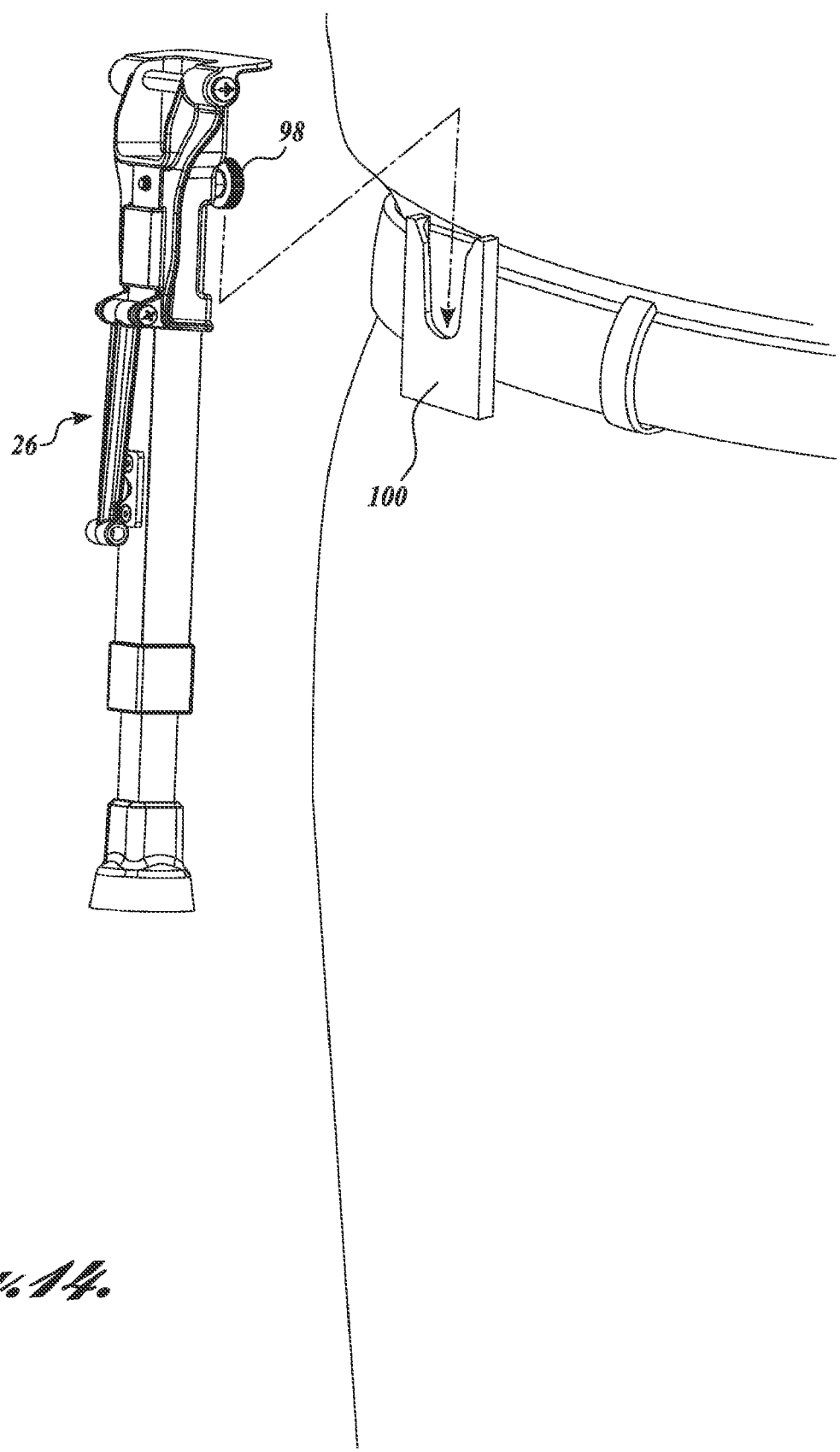

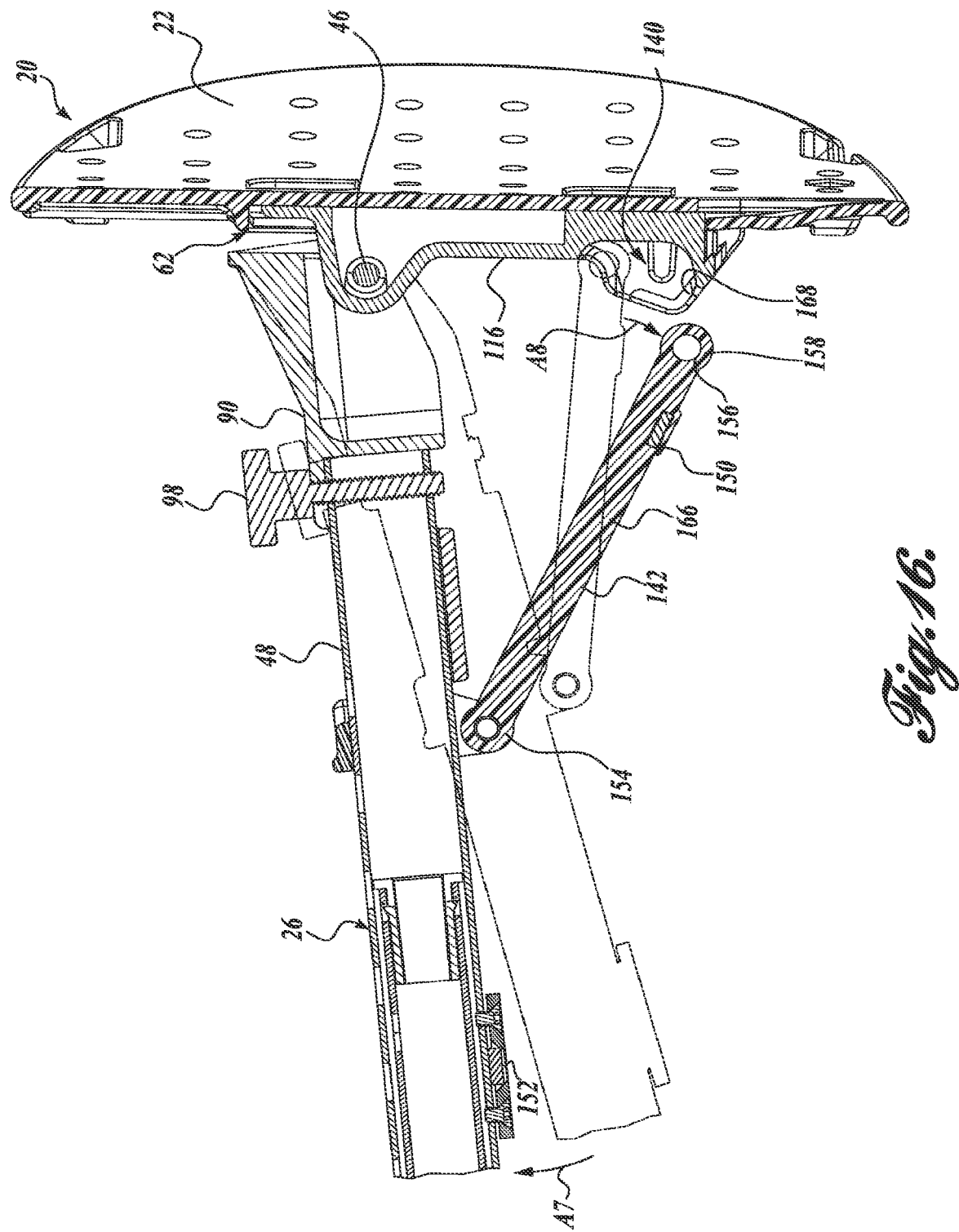

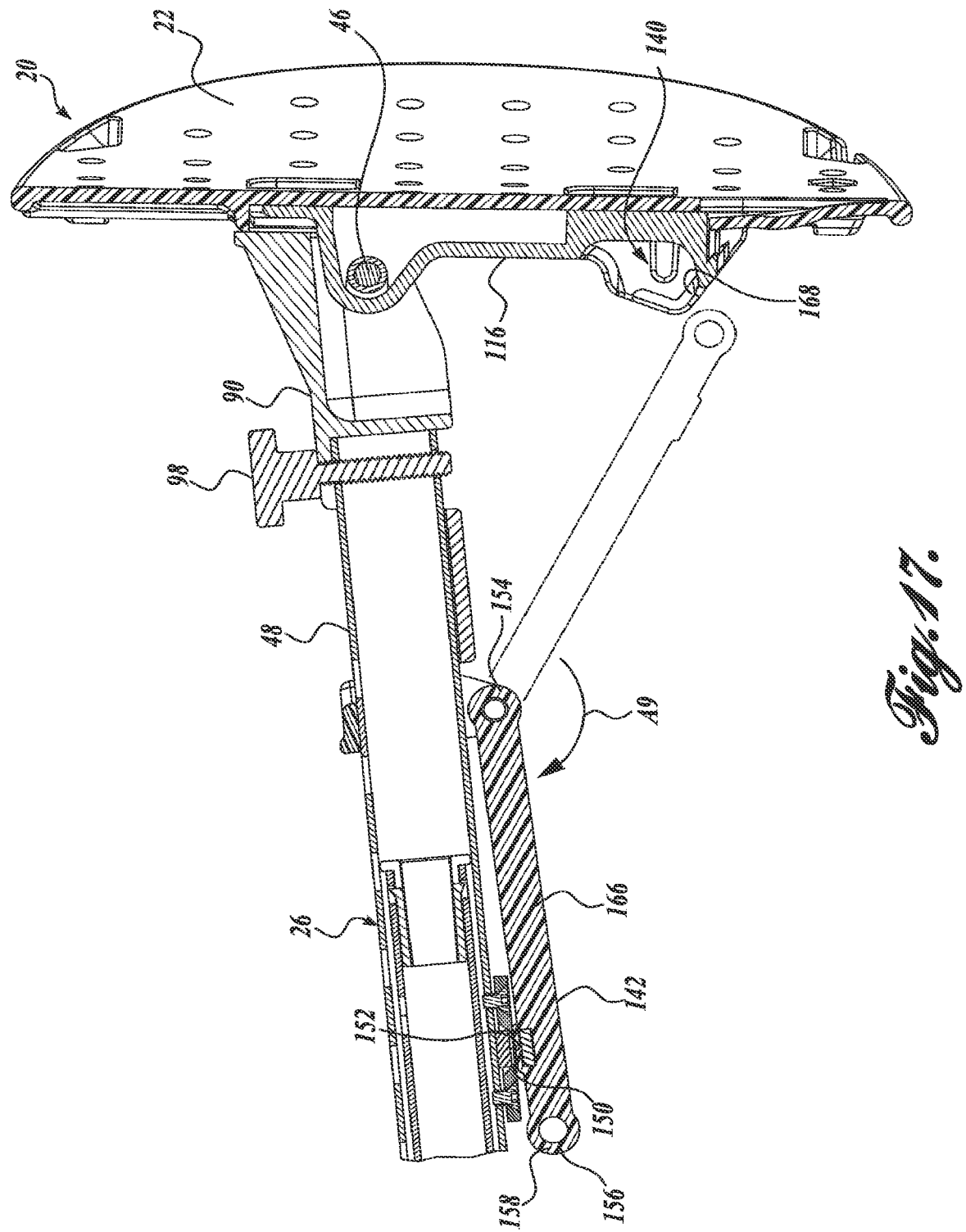

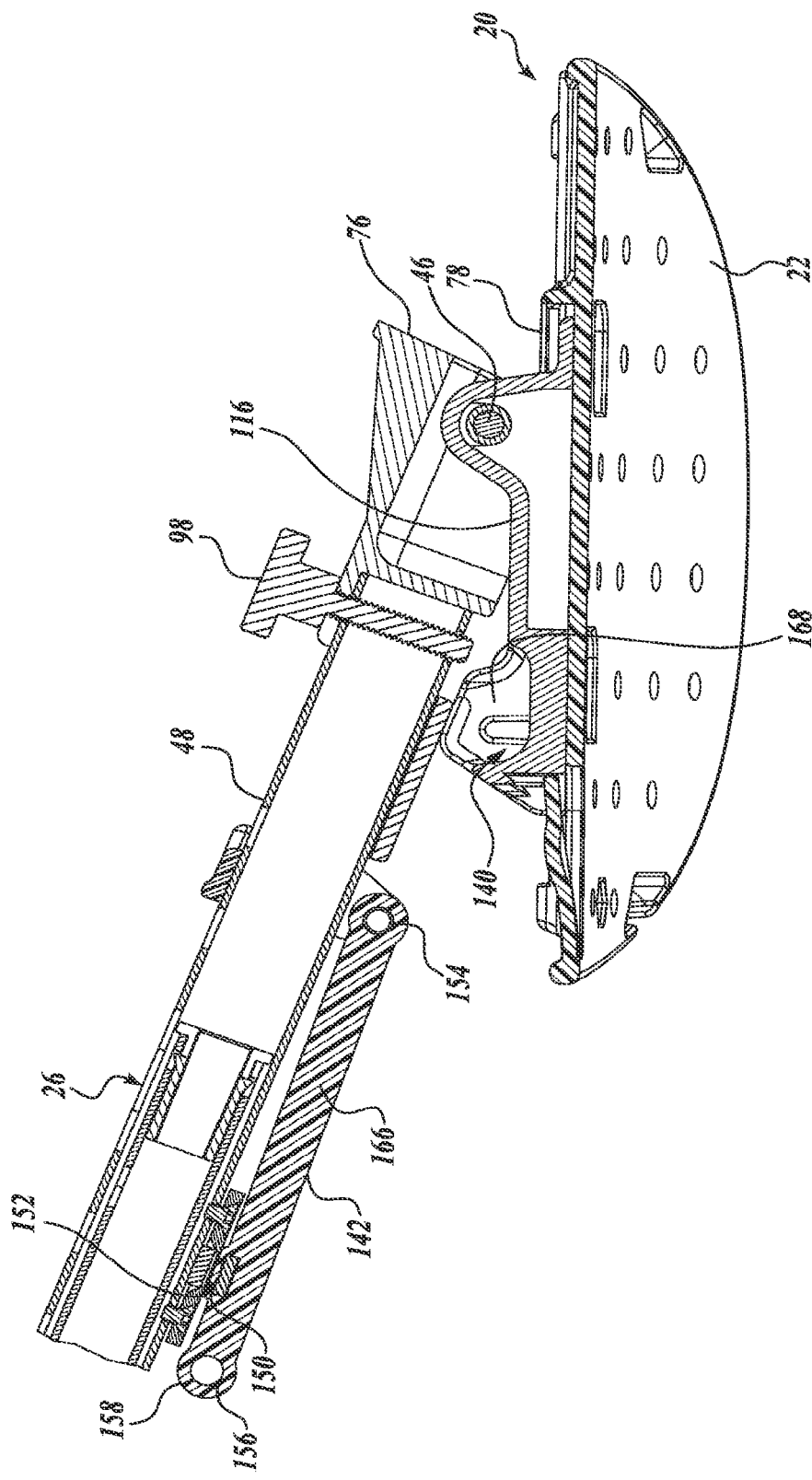

BODY SUPPORT DEVICE

CROSS-REFERENCE TO RELATED APPLICATION

This application is a continuation of U.S. application Ser. No. 16/738,952, filed Jan. 9, 2020, which claims the benefit of U.S. Provisional Application No. 62/790,325, filed Jan. 9, 2019, the disclosure of which is hereby expressly incorporated by reference herein in its entirety.

BACKGROUND

People who work on their hands and knees often suffer great lower back, knee, and wrist pain from long hours of working in that position. Therefore, there exists a need for a support device for working on hands and knees for daily work and also for people recovering from an injury.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with one embodiment of the present disclosure, a body support device is provided. The body support device includes: a body attachment portion having a first side and a second side, the first side including a plurality of receiving channels; and a leg assembly including an elongate member having an elongate body, a first end having a coupling interface configured for releasable attachment with the body attachment portion and a second end extending from the body attachment portion, wherein the coupling interface includes a hinge assembly having a first hinging portion and a second hinging portion, wherein the first hinging portion includes a plurality of protrusions configured for slidably releasable attachment in the plurality of receiving channels of the body attachment portion, and wherein the second hinging portion is configured for pivotal movement such that the elongate member is configured for movement between extended and retracted positions.

In accordance with another embodiment of the present disclosure, a body support device is provided. The body support device includes: a body attachment portion having a first side and a second side, the first side including a receiving section; and a leg assembly including an elongate member having an elongate body, a first end having a coupling interface configured for releasable attachment with the body attachment portion and a second end extending from the body attachment portion, wherein the coupling interface includes a hinge assembly having a first hinging portion and a second hinging portion, wherein the first hinging portion is configured for slidably releasable attachment in the receiving section of the body attachment portion, and wherein the second hinging portion is configured for pivotal movement such that the elongate member is configured for movement between extended and retracted positions, wherein the first hinging portion includes only a first knuckle, and wherein the second hinging portion includes second and third knuckles.

In accordance with another embodiment of the present disclosure, a body support device is provided. The body support device includes: a body attachment portion configured for attaching the body support device to a body of a user; a leg portion comprising an elongate member having an elongate body, a proximal end and a distal end, and a longitudinal axis extending along the first side of the leg portion, the proximal end of the leg portion configured for coupling with the body attachment portion, wherein the proximal end of the leg portion includes a continuous first stopping surface configured for contact with the body attachment portion, the first stopping surface having a first end and a second end, and wherein the distal end of the leg portion is configured to extend outwardly from the body attachment portion; and a coupling interface configured for hinged coupling of the leg portion to the body attachment portion, wherein the coupling interface includes a hinge at the first end of the first stopping surface of the leg portion, such that the leg portion is hingedly coupled to the body attachment portion and configured for hinging at a location spaced from the second end of the first stopping surface, wherein the first hinging portion includes only a first knuckle, and wherein the second hinging portion includes second and third knuckles.

In accordance with another embodiment of the present disclosure, a body support device is provided. The body support device includes: a body attachment portion having a first side and a second side, the first side including a receiving section; and a leg assembly including an elongate member having an elongate body, a first end having a coupling interface configured for releasable attachment with the body attachment portion and a second end extending from the body attachment portion, wherein the coupling interface includes a hinge assembly having a first hinging portion and a second hinging portion, wherein the first hinging portion is configured for slidably releasable attachment in the receiving section of the body attachment portion, and wherein the second hinging portion is configured for pivotal movement such that the elongate member is configured for movement between extended and retracted positions, and the leg assembly including a lock for locking the elongate member in a fixed position relative to the body attachment portion, the lock including a locking arm having a first end coupled to the second hinging portion and a second end configured to be received within a receiver on the first hinging portion.

In any of the embodiments described herein, the first hinging portion may include a leg assembly attachment portion.

In any of the embodiments described herein, the body attachment portion may include a leg assembly receiving portion.

In any of the embodiments described herein, the second hinging portion may include a leg receiving portion.

In any of the embodiments described herein, the leg receiving portion may include a sleeve.

In any of the embodiments described herein, the first hinging portion may include a first knuckle.

In any of the embodiments described herein, the second hinging portion may include second and third knuckles.

In any of the embodiments described herein, wherein the first hinging portion may include a first stopping surface.

In any of the embodiments described herein, the second hinging portion may include a second stopping surface for contacting the first stopping surface when the elongate member is in its extended position.

In any of the embodiments described herein, the first hinging portion may include a first bumping surface.

In any of the embodiments described herein, the second hinging portion may include a second bumping surface for contacting the first bumping surface when the elongate member is in its retracted position.

In any of the embodiments described herein, the pivotal movement of the elongate member may be restricted to a pivot range between 0 degrees and 90 degrees in a single plane perpendicular to the body attachment portion or a pivot range between 5 degrees and 85 degrees in a single plane perpendicular to the body attachment portion.

In any of the embodiments described herein, the leg assembly, when coupled to the body attachment portion, may be configurable in a fixed position for no pivotal movement of the elongate member relative to the body attachment portion.

In any of the embodiments described herein, the second end of the first stopping surface may be supported by a support.

In any of the embodiments described herein, the hinge may be configured such that the leg portion is pivotably coupled to the body attachment portion for movement between extended and retracted positions.

In any of the embodiments described herein, the body attachment portion may include a second stopping surface for interfacing with the first stopping surface of the leg portion.

In any of the embodiments described herein, the first stopping surface may be configured to mate with the second stopping surface when the leg portion is in the extended position.

In any of the embodiments described herein, the first stopping surface may be U-shaped, defining first and second side surface areas and a rear surface area.

In any of the embodiments described herein, the first side surface area may be adjacent the second knuckle and the second side surface area may be adjacent the third knuckle.

In any of the embodiments described herein, the second hinging portion may include a knuckle joiner between the second and third knuckles.

In any of the embodiments described herein, the knuckle joiner may include an arch extending between the second and third knuckles.

In any of the embodiments described herein, the knuckle joiner may include a reinforcement portion for supporting the arch.

In any of the embodiments described herein, the fixed position may be in the pivot range.

In any of the embodiments described herein, the fixed position may be in the range of degrees of 85 to 89 degrees in the pivot range.

In any of the embodiments described herein, the locking arm may include a head at the second end.

In any of the embodiments described herein, the receiver may receive the head in a cavity.

DESCRIPTION OF THE DRAWINGS

The foregoing aspects and many of the attendant advantages of the disclosed embodiments will become more readily appreciated as the same become better understood by reference to the following detailed description, when taken in conjunction with the accompanying drawings, wherein:

FIGS. 12 and 13 depict side views of the support device of FIG. 1 showing the range of motion of the leg portion between extended (FIG. 12) and retracted (FIG. 13) positions;

FIG. 14 is a perspective view of an attachment device for receiving a detached leg of the support device; and FIGS. 15-18 depict a side view of the support device depicted in FIG. 1 with the leg of the support device in an extended position and in a locked configuration and showing the process of unlocking the leg from the extended locked position.

DETAILED DESCRIPTION

Figure 1:
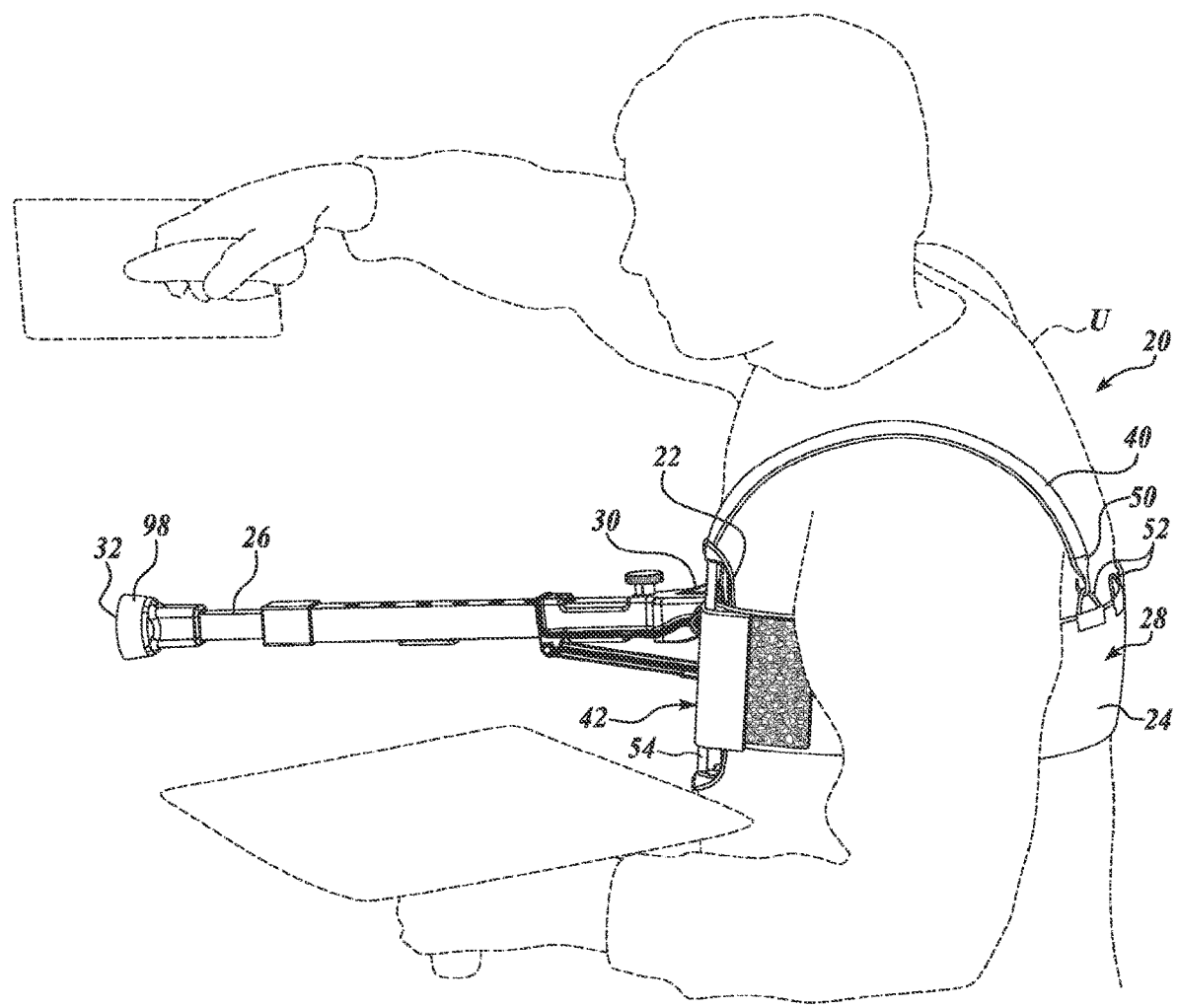
FIG. 1 depicts an embodiment of a user in an upright position and using a chest-mounted support device in an extended position, in accordance with the embodiments disclosed herein.

Embodiments of the present disclosure are directed to a chest-mounted body support device. In accordance with one embodiment of the present disclosure, a chest-mounted body support device 20 (or support device 20) can be seen in FIGS. 1-8. The support device 20 includes a body attachment portion 22, a body strap 24 configured to couple the body attachment portion 22 to a user U, and a leg assembly 26 having a proximal end 30 and a distal end 32. In the illustrated embodiment of FIGS. 1-8, the proximal end 30 of the leg assembly 26 is coupled to the body attachment portion 22 and the distal end 32 is configured to extend outwardly from the body attachment portion 22 and the body of the user U.

In the comparative configurations of FIGS. 9 and 10, the leg assembly 26 may be detachable from the body attachment portion 22, as described in greater detail below.

Figure 5:
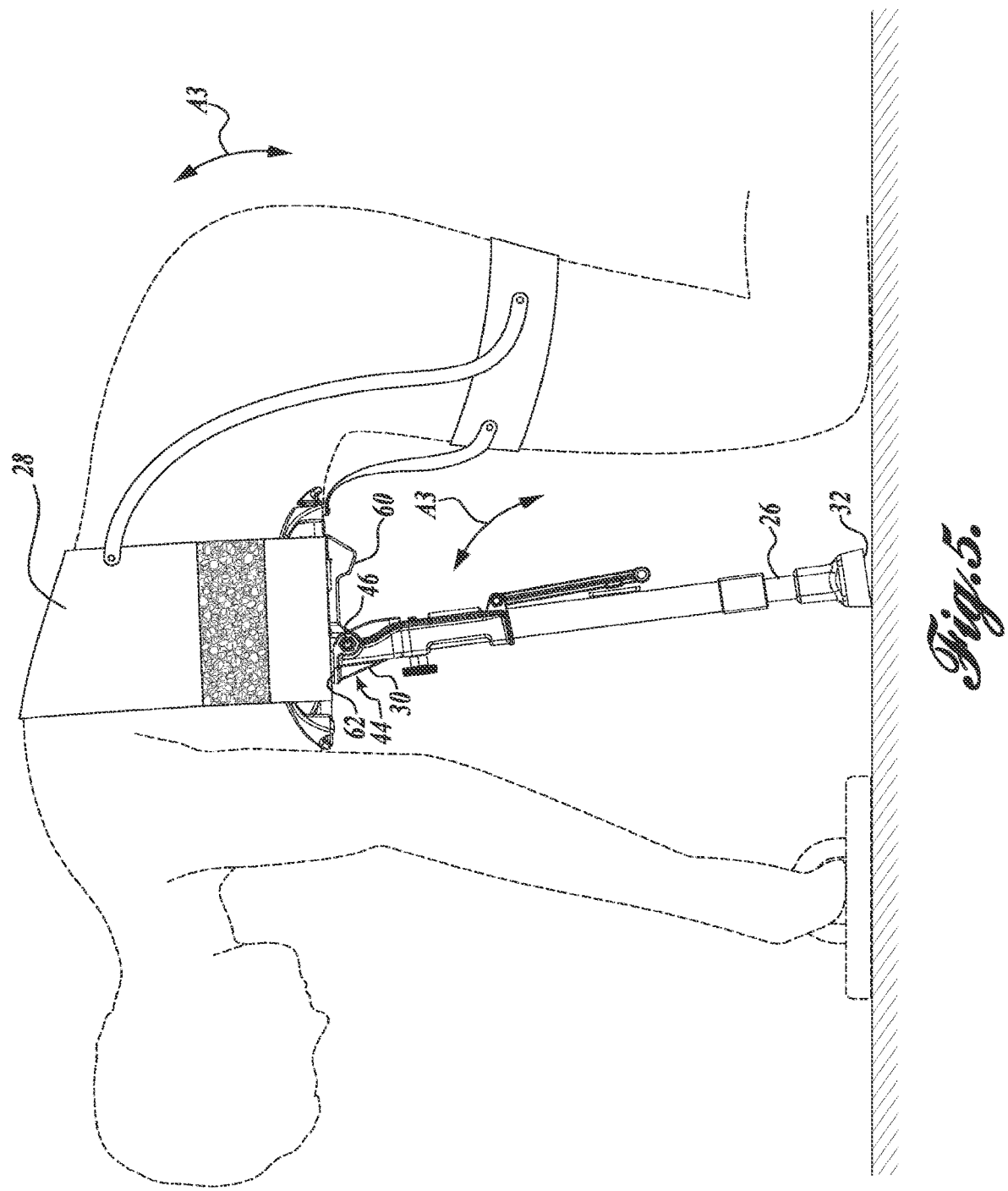
FIG. 5 depicts a side view of the user and the support device of FIG. 1, with the user in a kneeling position and the leg portion in an extended position.

The support device 20 is designed and configured to provide support of a user's upper body weight to alleviate stress and strain from the weight of the upper torso on the lower back, spine, knees, and muscles as well as evenly distributing body weight to at least three points when in a kneeling position (see FIG. 5, two knees and the chest of the user U). The support device 20 also frees up both hands for working. The support device 20 can also be used in an upright position, for example, to gain support from a wall (see FIG. 2). In general, the support device 20 helps alleviate the effects of constant weight loads on a user's body due to work or other demands.

The support device 20 may be used in any of a number of working applications including, but not limited to, flooring, painting, plumbing, carpentry, electrical, tile and masonry, mechanics, gardening, home and commercial cleaning, auto detailing, factory line work, agricultural work (e.g., harvesting), etc.

Language used in the present disclosure to depict orientation in the various illustrations (including as but not limited to top, bottom, front, rear, side, lateral, vertical, upward, downward, horizontal, and vertical), is provided for the reader's understanding with respect to the support device when in use as depicted in the drawings and is not intended to be limiting.

Figure 6:
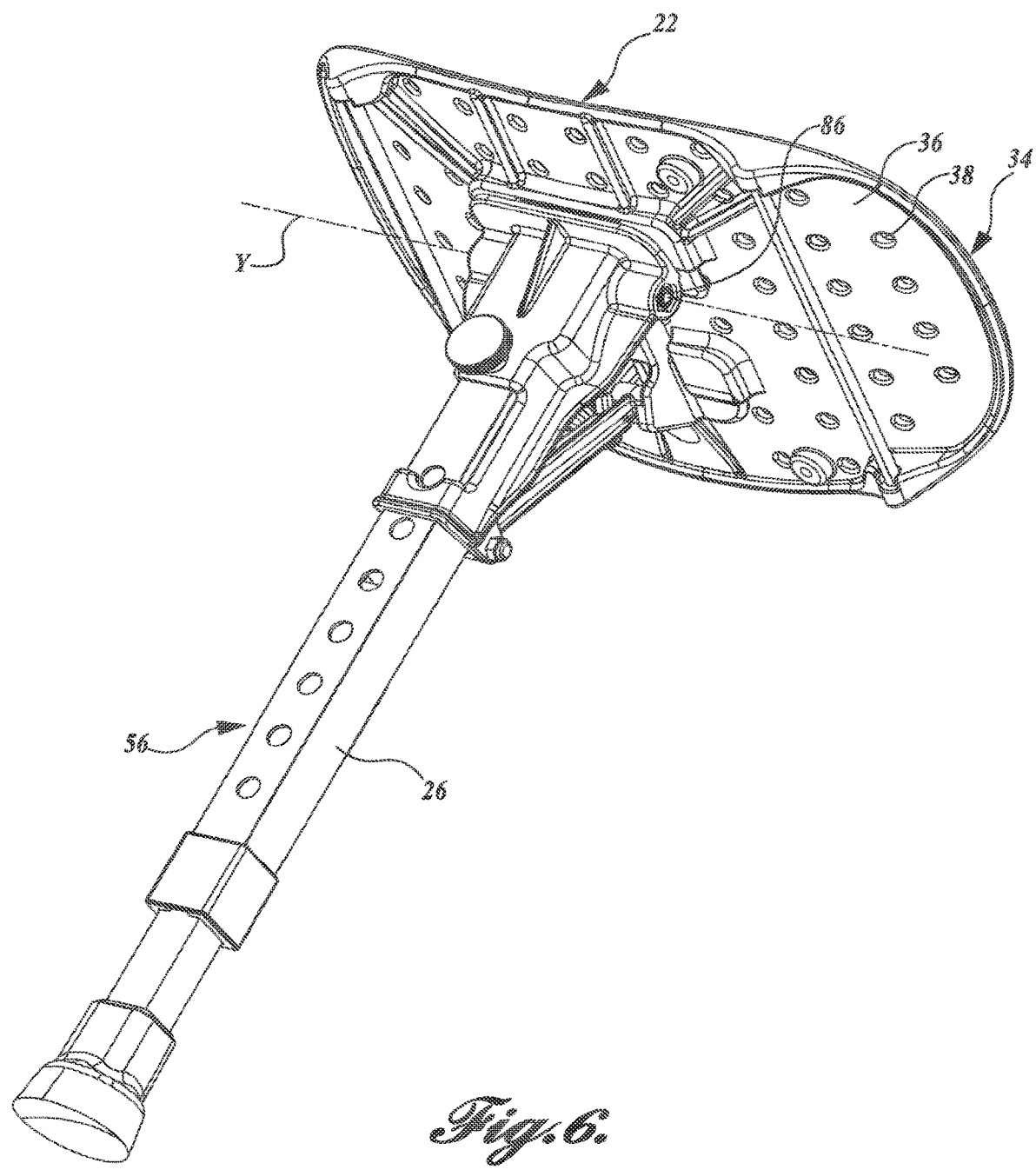
FIG. 6 depicts a front perspective view of the support device of FIG. 1 with the leg portion of the support device in an extended position and in a locked configuration.
Figure 7:
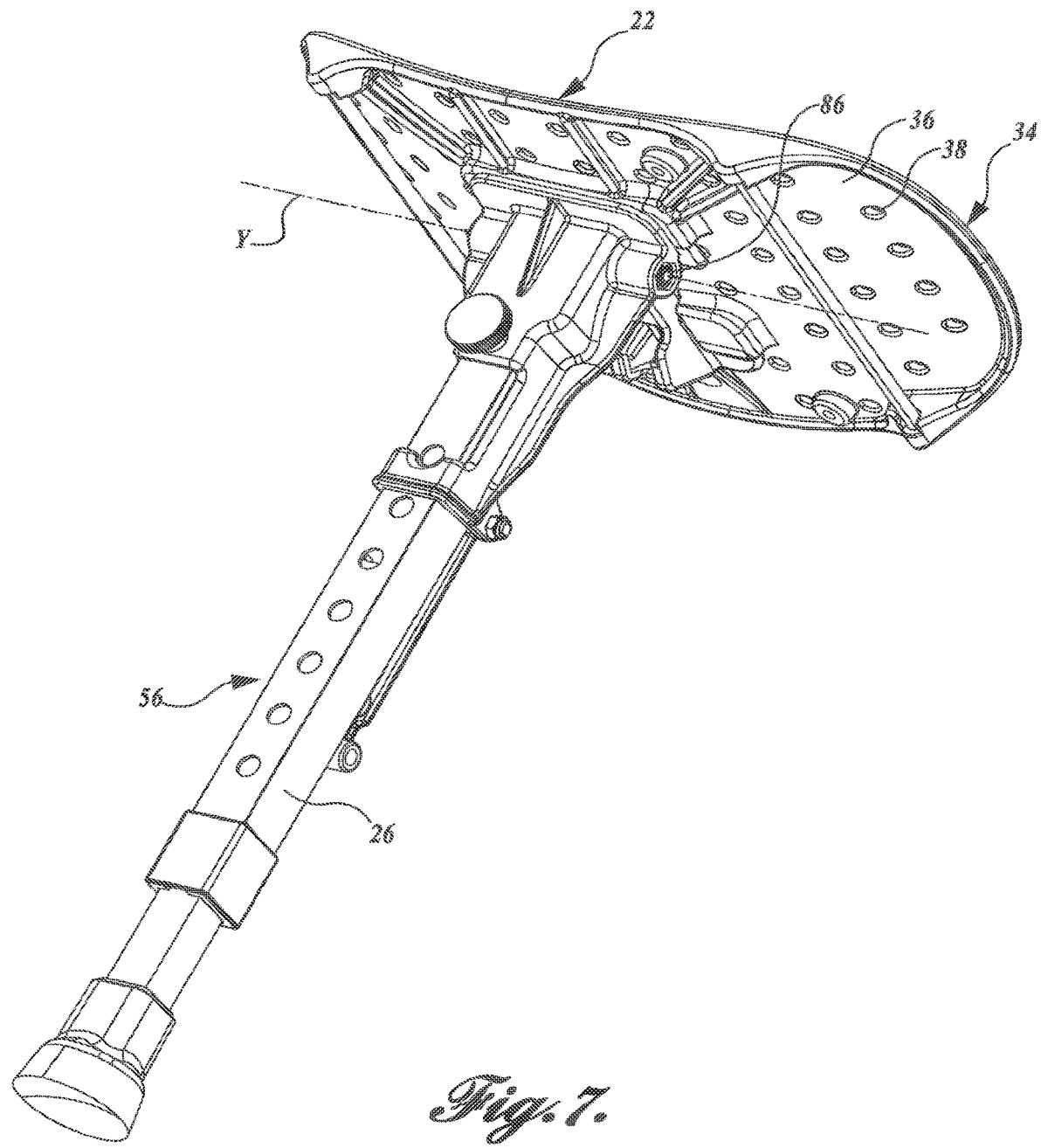
FIG. 7 depicts a front perspective view of the support device of FIG. 1 with the leg portion of the support device in an extended position and in an unlocked configuration.
Figure 8:
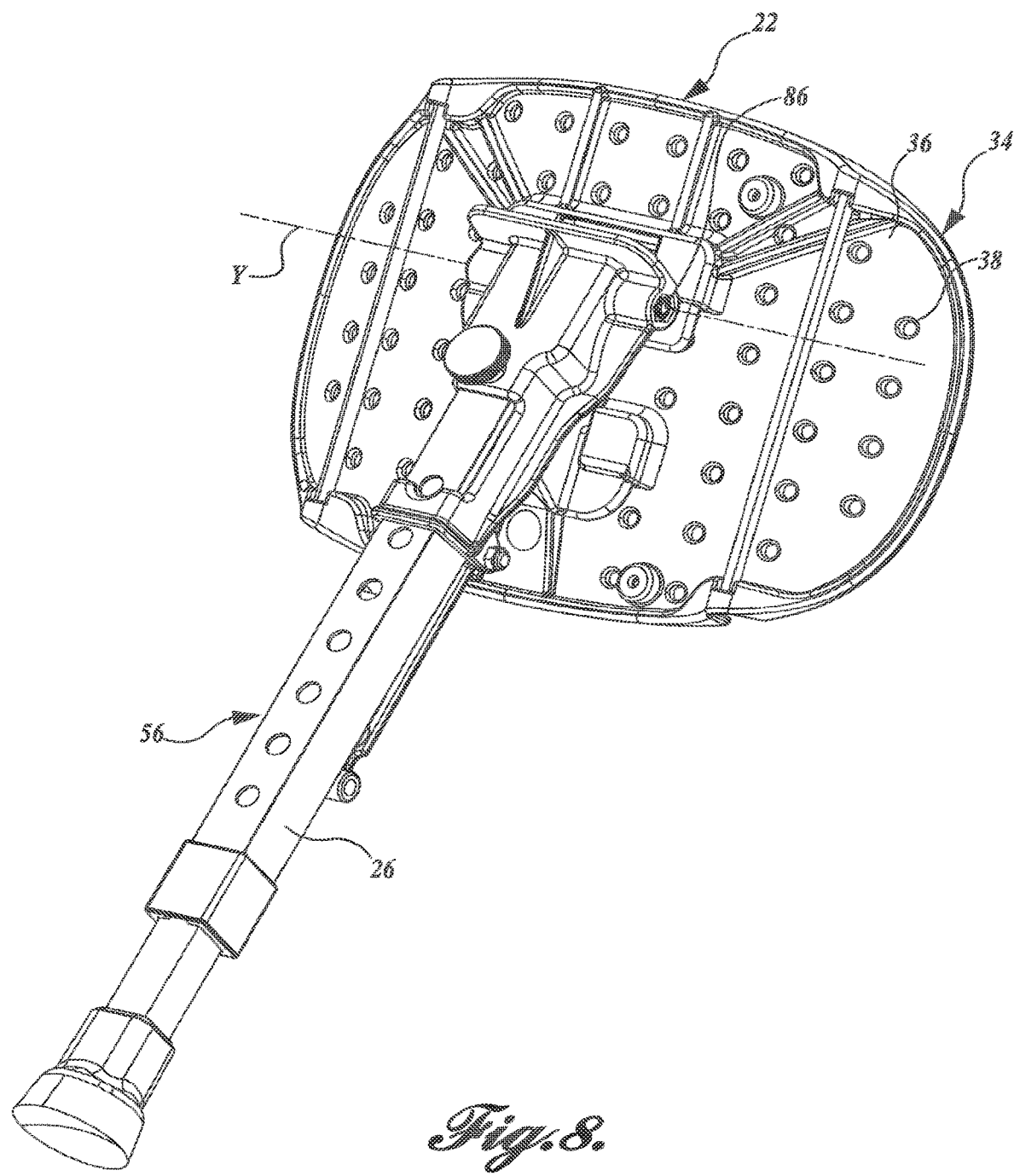
FIG. 8 depicts a front perspective view of the support device of FIG. 1 with the leg portion of the support device extending out at an angle from vertical in an unlocked configuration and without the user.

Referring to FIG. 1, the body attachment portion 22 (shown in the illustrated embodiment as a chest plate 22) may be a body shield or body support that is mounted on the user's body, which acts as a base support for the leg assembly 26 as it moves, as described in greater detail below. In the illustrated embodiment, the body attachment portion 22 is shown as a chest mounted body support. Referring to FIGS. 6-8, the body attachment portion 22 has a first side 34 and a second side 36. The first side 34 is designed for placement against the body of the user. The second side 36 is an outwardly extending side.

In one embodiment of the present disclosure, the first side 34 may include a padding material to provide comfort to the user. In one example, the padding material includes closed cell, high density foam with a thickness in a range from about 0.5 inches to about 2.0 inches. The first side 34 may be ergonomically conformed to the user's body. For example, the first side 34 may be contoured to fit securing against the contours of a human body. Likewise, the second side 36 may also be contoured to have a substantially uniform thickness along the cross section of the chest portion.

The second side 36 may be configured from a rigid material to provide structure to the body-mounted support device 20. For example, some or all portions of the second side 36 may be configured from a rigid plastic or metal material. The second side 36 may be integrally constructed, or may be formed from multiple components.

The body attachment portion 22 is sized to provide body support to a user U, whether the user U is in a standing, angled, or full horizontal position (for example, when a user is on hands and knees). In the illustrated embodiment, the body attachment portion 22 is designed to extend across most of the width of a user's chest and to have a near center point aligned with the sternum of the user. In some embodiments of the present disclosure, the body attachment portion 22 may be sized larger to provide additional body support for a user. For example, in a cement work application, the user U may want to rest his or her full body weight on the support device 20. In this application, a larger body attachment portion 22 may be advantageous.

In another example, in a standing application, the user U may want to rest his or her pelvis area on the body attachment portion 22. In this application, the body attachment portion 22 may be differently contoured to support the pelvis area in addition to the chest area or in lieu of the chest area.

In some embodiments of the present disclosure, the body attachment portion 22 and/or the padding material on the first side 34 may be contoured based on a gender of a user (e.g., based on female anatomy or male anatomy).

The body attachment portion 22 may have a series of holes 38 extending through the first side 34 and the second side 36 to provide breathability and comfort for the user U (see FIGS. 6-8).

As will be described below with reference to FIGS. 12 and 13, the body attachment portion 22 of the illustrated embodiment includes a portion of the coupling interface 44 configured to couple the leg assembly 26 to the body attachment portion 22 and to permit at least a portion of the leg assembly 26 to pivot when coupled to the body attachment portion 22.

Referring to FIG. 1, the body attachment portion 22 (shown in the illustrated embodiment as chest plate 22) attaches to the user's body. In the illustrated embodiment, a body attachment system 28 includes a body strap 24 used to wrap around the user's torso and attach the body attachment portion 22 to the user's body. The body strap 24 may be a flexible fabric strap for comfort and ease of use. The body strap 24 may be configured to have an adjustable length. Such adjustment may be achieved by belt buckles, hook and loop fasteners, clamp-type fasteners, or any other suitable adjustment mechanism. In the illustrated embodiment, the body attachment system 28 also includes a shoulder strap 40 used to provide additional stability of the body attachment portion 22 to the user's body (see FIG. 1).

To attach the shoulder strap 40, the body strap 24 includes a plurality of loops 82. A hook fastener 50 on the shoulder strap is configured to be fastened to one of the plurality of loops 52. The user U may fasten the hook fastener 50 to a particular one of the plurality of loops 52 depending on the size of the user's chest.

The shoulder strap 40 may carry little or no load during use of the support device 20. However, the shoulder strap 40 can provide support to the support device 20 while the user is putting on the support device 20 and/or when the user is in a sitting position.

For the illustrated embodiment and as a non-limiting example, the body attachment portion 22 in described herein as a chest plate or a chest attachment portion 22 because it is configured to be located on the user's chest to align with the user's sternum. However, in other embodiments, the body attachment portion may be configured to be located on other parts of the user's body, for example, to align with the user's pelvic bones or with the leg of the user. Therefore, the use of the term chest plate with reference to the illustrated embodiment is not to be construed as limiting.

Referring to FIG. 1, the body strap 24 is attached to the chest plate 22 by a strap attachment portion 42. In the illustrated embodiment, the strap attachment portion 42 includes two rods 54 positioned outwardly from the second side 36 of the chest plate 22 (see FIGS. 9 and 10). The rods 54 are oriented substantially vertical when the user U is standing vertically (see FIG. 2). One end of the body strap 24 slides between a first rod 54 and the second side 36 of the chest plate 22, wraps around the first rod 54, and is secured to another portion of the body strap 24. The other end of the body strap 24 is secured around a second rod 54 in similar fashion. The rods 54 are positioned outwardly from the second side 36 of the chest plate 22 to provide leverage for the user when fitting the body strap 24 to the user's body. The rods 54 allow the body strap 24 to be pulled tightly to create a snug fit of the chest plate 22 against the user's body. The rods 54 may be coupled to or molded into the chest plate 22.

Although the strap attachment portion 42 is shown as two rods 54, the strap attachment portion 42 may include just one rod. In such an embodiment, one end of the body strap 24 may be fixed to one side of the chest plate 22 and the other end of the body strap is capable of adjustment to the single rod on the other side of the chest plate 22. Other embodiments of body attachment portions are also within the scope of the present disclosure. For example, the body strap may be received in longitudinal slots extending through the chest plate.

The shoulder strap 40 may be used to help maintain the positioning of the chest plate 22 on the user's body. In the illustrated embodiment, one end of the shoulder strap 40 is attached to the second side 36 of the chest plate 22 and the other end of the shoulder strap 40 is attached to the body strap 24. In one embodiment, the point at which the shoulder strap 40 attached to the body strap 24 is adjustable along the length of the body strap 24 to accommodate users of different sizes.

In other embodiments of the body attachment system 28, one or more leg straps (see, for example, FIG. 5) may be used to further maintain the positioning of the chest plate 22 on the user's body.

In the illustrated embodiment of FIGS. 2-5, the leg assembly 26 has a coupling interface 44 configured to couple the leg assembly 26 to the chest plate 22 and to permit at least a portion of the leg assembly 26 to pivot when coupled to the chest plate 22. In one embodiment, when the leg assembly 26 is coupled to the chest plate 22 and the user U is standing vertically (see FIG. 2), the coupling interface 44 permits at least a portion of the leg assembly 26 to pivot about a pivot axis (see axis Y in FIGS. 6-8) through the coupling interface 44 (see hinge assembly 46) and substantially parallel to the chest plate 22. In other words, the coupling interface 44 permits at least a portion of the leg assembly 26 to pivot about hinge assembly 46 in a plane that is substantially perpendicular to the chest plate 22, as indicated by arrows A1 and A2 in respective FIGS. 3 and 4. In one embodiment, at least a portion of the leg assembly 26 is configured to pivot relative to the chest plate 22 in a pivot range. In one embodiment, the pivot range is between 0-degrees from vertical (i.e., with the leg 26 pointed directly down when the user is standing) and about 90-degrees from vertical. In another embodiment, the range is between about 5-degrees from vertical (i.e., the position shown in FIG. 4 with the leg 26 not entirely pointed down when the user is standing) and about 85-degrees from vertical (i.e., the position shown in FIG. 3 with the leg assembly 26 nearly perpendicular to the rods 54 of the chest plate 22). A bumper system 60 and a stop system 62 described in greater detail below (see FIGS. 12 and 13), are used to control the pivot range of the leg assembly 26 relative to the chest plate 22.

Figure 2:
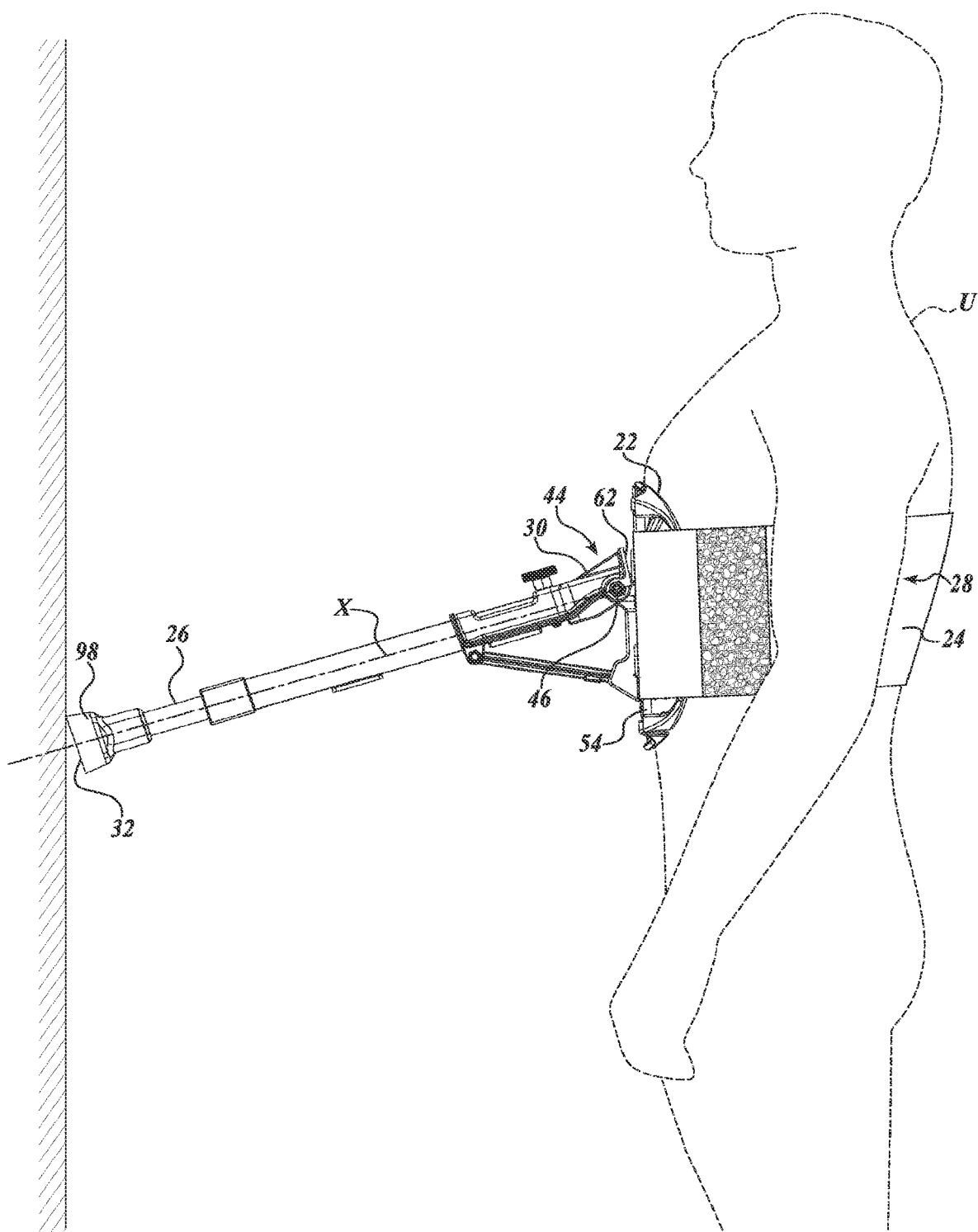
FIG. 2 depicts a side view of the user and the support device of FIG. 1, with the leg portion of the support device in an extended position and in a locked configuration.

Referring to FIG. 5, during usage of the support device 20, the hinged attachment of the leg assembly 26 to the chest plate 22 allows for rocking motion of the user's body on the leg portion 70 of the leg assembly 26 when the support device 20 is supporting the user and when the leg assembly 26 is not in a locked position (compare locked position in FIG. 2, which does not allow rocking motion). Such rocking motion (as indicated by two arrows labeled A3 in FIG. 5) allows the user to move into different working positions while still being supported by the leg assembly 26. The rocking motion is limited by the pivot range of the leg assembly 26 relative to the chest plate 22 between the bumper 60 and the stop 62, as will be described in greater detail below.

In some embodiments, the coupling interface 44 on the chest plate 22 is located such that the movable portion 48 of the leg assembly 26 and/or the pivot axis of the movable portion 48 of the leg assembly 26 are in particular locations to provide balanced support to the user and to align the coupling interface 44 with the sternum of the user for maximum support. In one embodiment, the coupling interface 44 is configured such that the pivot axis is horizontally centered on the chest plate 22. In another embodiment, the coupling interface 44 is configured such that the pivot axis is vertically centered on the chest plate 22. In yet another embodiment, the coupling interface 44 is configured such that the pivot axis is located vertically at a position between the center of the chest plate and three fourths of the distance from the bottom of the chest plate 22 to the top of the chest plate 22. Locating the pivot axis vertically above the center of the chest plate 22 may help provide a balance point for the user in a kneeling position so as to avoid falling face-first over the top of the leg 26 (see balance in FIG. 5).

In the illustrated embodiment, the coupling interface 44 between the leg assembly 26 and the chest plate 22 includes a detachable mechanism to allow for detachment of the leg assembly 26 from the chest plate 22 (see FIGS. 9 and 10), as will be described in greater detail. However, in other embodiments of the present disclosure, the leg 26 may not include a system for quick detachment from and reattachment to the chest plate 22.

Referring to the exploded view of FIG. 11, the leg assembly 26 of the illustrated embodiment will now be described in greater detail. The leg assembly 26 includes multiple components, including a leg portion 70, a leg receiving portion 72, a leg attachment portion 74 for attaching the leg assembly 26 to the chest plate 22, and the hinge assembly 46 for allowing hinged movement between the leg receiving portion 72 and the leg attachment portion 74. Referring to FIGS. 12 and 13, the leg assembly 26 includes a first stopping surface 76 designed for interfacing with a second stopping surface 78 on the chest plate 22 (see FIG. 13), defining stop 62 (see FIG. 12). Further, the leg assembly 26 defines a first bumping surface 80 (see FIG. 12) designed for interfacing with a second bumping surface 82, defining bumper 60 (see FIG. 13).

Returning to FIG. 11, in the illustrated embodiment, the leg receiving portion 72 at the proximal end 30 of the leg assembly 26 includes a sleeve 90 for receiving a separate leg portion 70 component. In the illustrated embodiment, the leg portion 70 can be slidably received within the sleeve. The leg portion 70 can be secured within the sleeve 90 by fastener 92, As seen in FIGS. 12 and 13, together, the leg portion 70 and the leg receiving portion 72 define the pivoting leg portion 48 of the leg assembly 26. The pivoting leg portion 48 of the leg assembly 26 has a first side 186 and a second side 188.

Returning to FIG. 11, in the illustrated embodiment, the fastener 92 securing the leg portion 70 within sleeve 90 is configured to extend through hole 94 in the sleeve 90 and hole 96 in the leg portion 70. However, other fastening configurations are within the scope of the present disclosure. In the illustrated embodiment, the fastener 64 is a knob fastener, which works in conjunction with a leg receiving device 100 when the leg assembly 26 is detached from the chest plate 22 (see FIG. 14, as described in greater detail below.)

In the illustrated embodiment, the knob fastener 64 is located on the second side 188 of the pivoting leg portion 48 of the leg assembly 26 to orient the leg assembly 26 on the user's body (for example, on the user's belt) with minimal interference to the user U. However, the fastener may be configured in other orientations to secure the leg portion 70 within sleeve 90 for interfacing with the leg receiving device 100 (see FIG. 14) in another orientation.

In the illustrated configuration, the leg portion 70 and the sleeve 90 may be made from different materials for enhancing various properties of the support device 20. For example, the leg portion 70 may be made from metal, such as aluminum, for strength properties and weight reduction, and the sleeve 90 may be made from a molded plastic for manufacturing advantages. In other embodiments of the present disclosure, the pivoting leg portion 48 of the leg assembly 26 may be an integrally manufactured component including both the leg portion 70 and the sleeve 90.

The sleeve 90 may designed to include features to optimize the hinge assembly 46 components of the leg assembly 26, the stopping surface 78 and the bumping surface 82 of the leg assembly 26 defining the bumper 60 and the stop 62, and the leg locking components, all described in greater detail below.

Still referring to FIG. 11, the hinge assembly 46 of the leg assembly 26 will now be described in greater detail. The hinge assembly 46 includes first and second hinging portions 102 and 104. The first hinging portion 102 is either attached to the chest plate 22 or configured to be attached to the chest plate 22. The second hinging portion 104 is part of the pivoting leg portion 48 of the leg assembly 26.

The first and second hinging portions 102 and 104 define a knuckle assembly 106. In the illustrated embodiment, the knuckle assembly 106 includes knuckles 170, 172, and 174 joined by pin 108. Pin sleeve 110 holds pin 108 in the knuckles 170, 172, and 174. In the illustrated embodiment, the first hinging portion 102 includes one knuckle, shown as a first knuckle 170, and the second hinging portion include second and third knuckles 172 and 174. The second and third knuckles 172 and 174 are configured to surround the first knuckle 170 on both sides of the first knuckle 170 when mated by pin 108.

In the illustrated embodiment, the length of the first knuckle 170 is longer than the lengths of the respective second and third knuckles 172 and 174 to provide strength to the first knuckle 170. As a non-limiting example, in the illustrated embodiment the length of the first knuckle 170 is about two times the length of the second and third knuckles 172 and 174.

Figure 9:
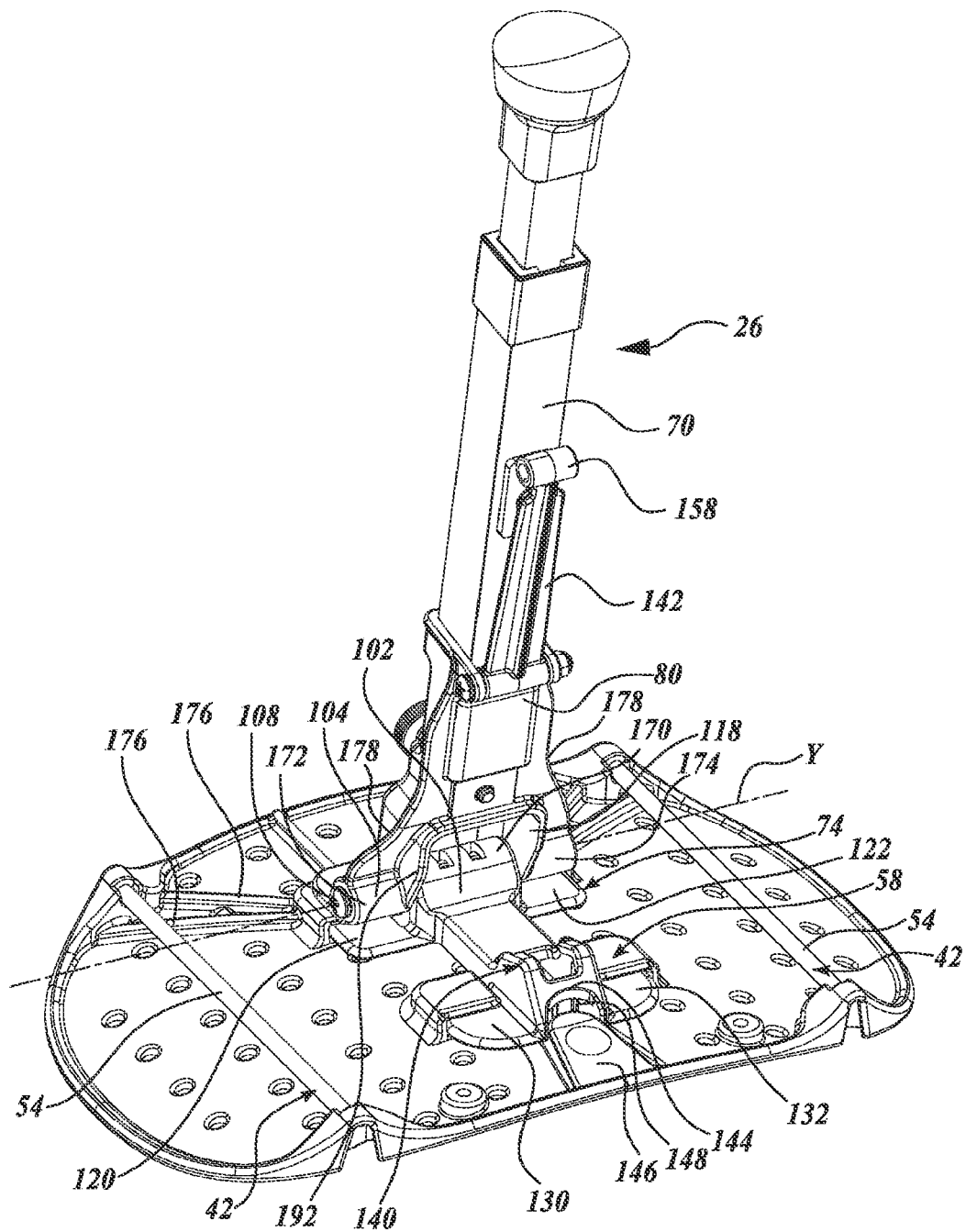
FIGS. 9 and 10 depict a back perspective view of the support device of FIG. 1 showing the process of detaching the leg assembly from the chest plate.
Figure 10:
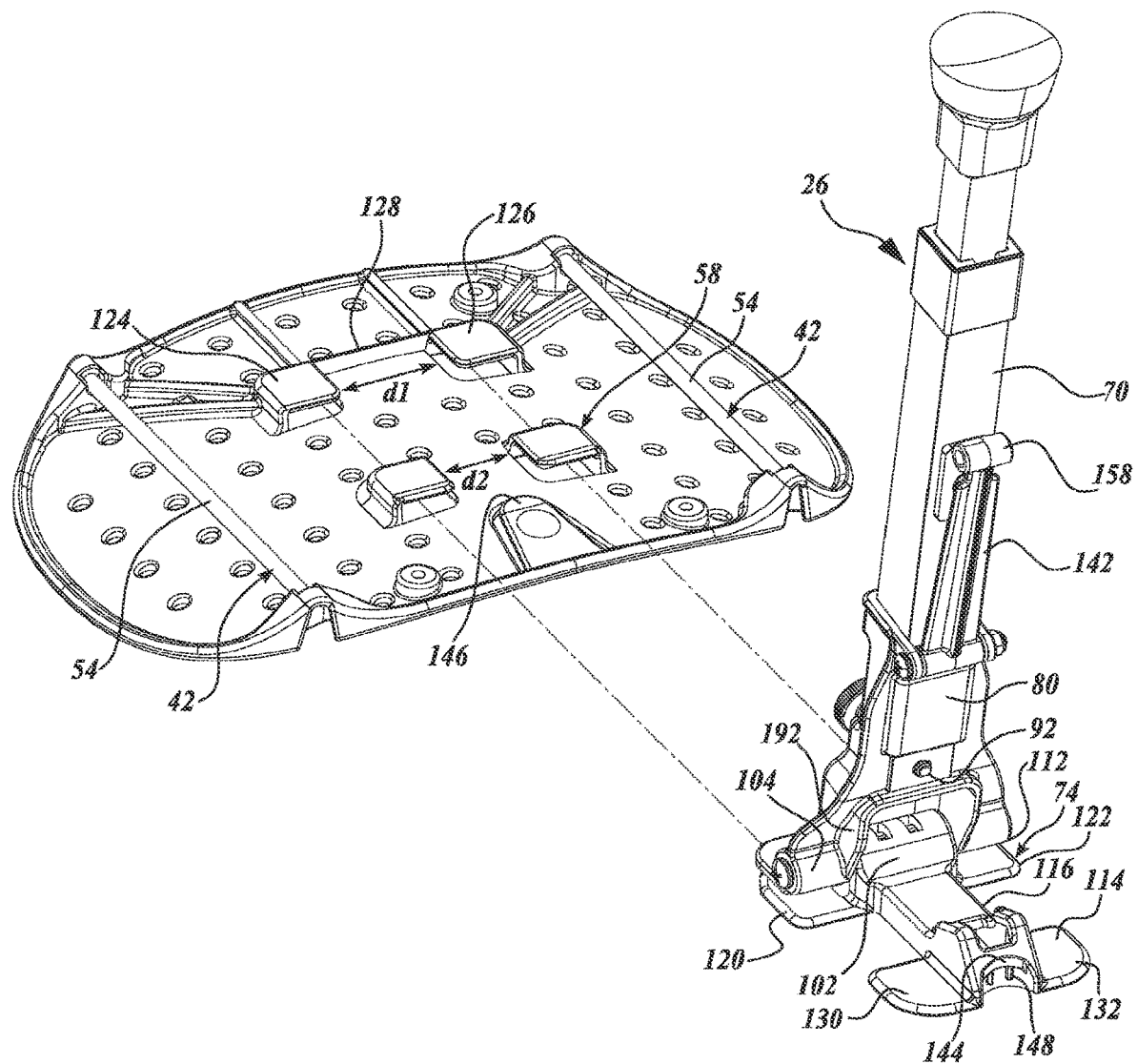

Referring to FIGS. 9 and 10, a rear-side view of the coupling of the first and second hinging portions 102 and 104 and the knuckle configuration is shown. As described above, the second and third knuckles 172 and 174 are configured to surround the first knuckle 170 on both sides of the first knuckle 170 when mated by pin 108. The first and second knuckles are a part of the pivoting leg portion 48 of the leg assembly 26. The knuckle assembly 106 extends to a width that is wider than the width of the leg portion 70 of the leg assembly 26. Such width distributes the loads on the leg portion 70 to a wider distribution zone on the chest plate 22.

A rib or flare system 176 on the chest plate help to further disperse the loads to a wider distribution zone on the chest plate 22, and particularly to the reinforced outer region of the chest plate 22. In the illustrated embodiment, the rib or flare system 176 includes a plurality of ribs extending upwardly and diagonally from a central region on the chest plate 22 to two outer corner regions of the chest plate 22. In the illustrated embodiment, the outer corner regions of the chest plate 22 are the upper outer corner regions when the chest plate 22 is positioned the chest of a user (see FIG. 1). However, other rib or flare systems are within the scope of the present disclosure.

The second and third knuckles 172 and 174 are joined in the pivoting leg portion 48 of the leg assembly 26 at a knuckle joiner 118 on sleeve 90, shown as an arch or bridge (see FIG. 9). The knuckle joiner 118 provides strength and load distribution to the knuckle configuration and to the pivoting leg portion 48 of the leg assembly 26. In the illustrated embodiment, the knuckle joiner 118 includes side reinforcements 178 for further support when the support device 20 is used in side leaning configurations (see FIG. 11). In addition, the knuckle joiner 118 further includes rear reinforcement 192 for further arch support (see FIGS. 12 and 13). On the front side, support 190 for the first stopping surface 76 (see FIGS. 12 and 13) provides further support to the knuckle joiner 118.

Figure 11:
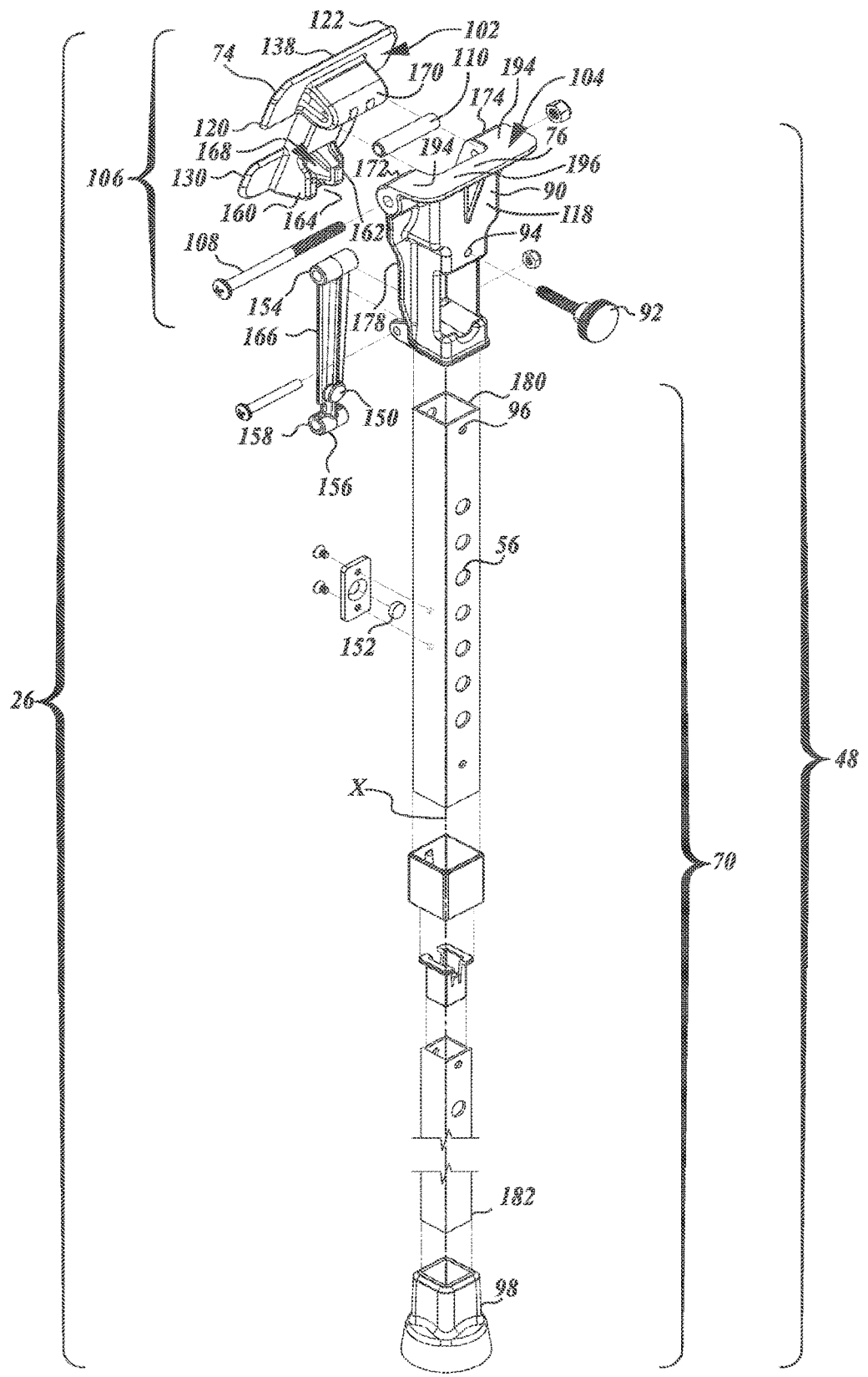
FIG. 11 is an exploded view of the leg assembly, the movable portion, the leg portion, and the knuckle assembly.

As seen in the exploded view of FIG. 11, the leg portion 70 of the leg assembly 26 may include a telescoping leg that permits the outwardly extending length of the leg assembly 26 to be adjusted. However, the leg portion 70 may also have a fixed length. One benefit to the telescoping leg is that it permits the user U to adjust the length of the leg portion 70, as may be preferable depending on the particular use of the support device 20. For example, the user U may prefer a first length of the leg portion 70 when standing vertically with the leg portion 70 against a wall (as illustrated in FIG. 2) and a different length when positioned horizontally with the leg portion 70 braced against the ground (as illustrated in FIG. 5).

In the illustrated embodiment, the length of the leg portion 70 can be adjusted by a telescoping leg adjustment system 56 shown as a button and hole depression system to secure the leg portion 70 at various lengths (see FIG. 6). Other length adjustment systems are also within the scope of the present disclosure.

The pivoting leg portion 48 of the leg assembly 26 can be configured to extend outwardly from the chest plate 22 and, when the chest plate 22 is worn by a user, to extend outwardly from the body of the user U.

Restrictions on the hinged movement of the pivoting leg portion 48 of the leg assembly 26 relative to the chest plate 22 will now be described. As seen in FIG. 11, the leg portion 70 of the leg assembly 26 is an elongate member having an elongate body and a central longitudinal axis X extending from the first end 30 of the leg portion 70 to the second end 32 of the leg portion 70. Referring to FIGS. 12 and 13, the hinge assembly 46 allows for restricted hinged movement of the leg portion 70 relative to the chest plate 22 between the bumper 60 (FIG. 13) and the stop 62 (FIG. 12). The leg portion 70 hingedly moves between the first position of FIG. 12, which is a leg extended position, and the second position of FIG. 13, which is a leg retracted position. (See also first position in FIG. 2 and second position in FIG. 3).

The stopping and bumping surfaces of the leg assembly 26 defining the bumper 60 and the stop 62 will now be described in greater detail. In the first position (FIG. 12), the first stopping surface 76 of the movable portion 48 of the leg assembly 26 mates with a second stopping surface 78 of the chest plate 22. In the second position (FIG. 13), the first stopping surface 76 of the movable portion 48 of the leg assembly 26 is rotated out of contact the second stopping surface 78 disposed on the chest plate 22. In the second position, the first bumping surface 80 on the movable portion 48 of the leg assembly 26 interfaces with a second bumping surface 82 disposed on the chest plate 22.

In the illustrated embodiment, second stopping surface 78 and the bumping surface 82, both disposed on the chest plate 22, are part of the leg attachment portion 74 of the leg assembly 74 that is coupled to the chest plate 22. However, in other embodiments of the present disclosure, the second stopping surface 78 and the bumping surface 82 may be disposed directly on the chest plate 22 than the cross-sectional area of the leg portion 70 of the leg assembly 26.

While shown in the illustrated embodiment as generally planar surfaces, either of the stopping surfaces 76 or 78 may be angled to reduce or increase the pivot range of the leg assembly 26. Likewise, either of the stopping surfaces 76 or 78 may be contoured to enhance the interface between the surfaces.

Referring to FIGS. 12 and 13, the first stopping surface 76 extends laterally from the end of the movable portion 48 of the leg assembly 26 between first and second ends 84 and 86. As seen in FIG. 11, the first stopping surface 76 is a single continuous surface. In the illustrated embodiment, the first stopping surface 76 is designed and configured to align with the knuckles portions 172 and 174 of the second hinging portion 104. As seen in FIG. 11, the first stopping surface 76 is U-shaped, defining side surface areas 194 and a rear surface area 196. In that regard, the side surface areas 194 of the first stopping surface 76 are adjacent and coupled to the second and third knuckles 172 and 174 of the second hinging portion 104 and includes a space to receive the first knuckle 170 of the first hinging portion 102. The rear surface 196 of the first stopping surface 76 is adjacent the first knuckle 170 of the first hinging portion 102.

The U-shape of the first stopping surface 76 provides for enhanced support of the moveable leg assembly 26, particularly when in the extended position of FIG. 12. Although the pivotal movement of the leg assembly 26 is generally within a pivot range in a single plane perpendicular to the chest plate 22, sometimes the user can flex the leg assembly 26 sideways when moving the leg assembly 26 in the plane. Because the rotation of the user's body, particularly when in the hands and knees position of FIG. 5, may not always be exactly following the plane of the motion of the leg assembly 26 as indicated by arrow A3, the side surface areas 194 of the first stopping surface 76 provide side support when the user flexes the leg assembly 26 to the side or rocks side-to-side when pivoting the leg assembly 26 generally in the motion of arrow A3 shown in FIG. 5.

When the user is in a position such that the leg assembly 26 of the support device 20 is in the fully expended position shown in FIG. 5 (see also FIG. 12), the side surface areas 194 and the rear surface 196 of the first stopping surface 76 provide a stable surface upon which the user may support his or her body.

The knuckle assembly 106 works in concert with the U-shaped stopping surface 76 to further provide support to the user when the user rocks side-to-side as the user moves pivots on leg assembly 26 generally in the motion of arrow A3 shown in FIG. 5. In that regard, the second and third knuckles 172 and 174 provide outer stability and support to each of the side surface areas 194 of the first stopping surface 76. If the knuckle assembly 106 was a two-knuckle or a four-knuckle assembly, only one of the side surface areas 194 of the U-shaped stopping surface 76 would be supported by the outer knuckles, causing reduced stability for the user on one side.

In the illustrated embodiment, the first stopping surface 76 is supported by a first stopping extension section 184 (see FIGS. 12 and 13) which extends beyond the second side 188 of the movable portion 48 of the leg assembly 26 and is supported by a stopping section support 190 extending from the second side 188 of the movable portion 48 of the leg assembly 26 to the stopping extension 184. In other embodiments, the first stopping extension section 184 may be supported by a plurality of supports.

The hinge assembly 46 and the pivot axis of the leg assembly 26 through the hinge assembly 46 (see axis Y in FIGS. 6-8) is located at the first end 84 of the stopping surface 76 adjacent the first stopping surface 76. The hinge assembly 46 allows for hinged movement of the movable portion 48 of the leg assembly 26 between extended and retracted positions relative to the chest plate 22 within the pivot range in a single plane perpendicular to the chest plate 22 (see arrows A4 and A5 in respective FIGS. 12 and 13).

In the illustrated embodiment, the first stopping surface 76 is not centered on the central axis (see axis X in FIGS. 12 and 13) of the leg portion 70. In contrast, the first stopping surface 76 is laterally offset from the central axis (see axis X in FIGS. 12 and 13) of the leg portion 70 such that a center point on the second end 86 of the first stopping surface 76 (see FIG. 11) is spaced a distance d3 from the central axis X of the leg portion 70. In the illustrated embodiment, the first stopping surface 76 is adjacent the central axis (see axis X in FIGS. 12 and 13) of the leg portion 70. By laterally offsetting the first stopping surface 76 from the central axis X of the leg portion 70, the hinge assembly 46 and the pivot axis of the movable portion 48 of the leg assembly 26 through hinge assembly 46 (see axis Y in FIGS. 6-8) can be positioned at or near the central axis X of the leg portion 70. Accordingly, the movable portion 48 of the leg assembly 26 is configured for hinging at a location spaced from a center point on the second end 86 of the first stopping surface 76.

Such positioning of the hinge assembly 26 the central axis X of the leg portion 70 may enhance the stability of the leg portion 70 and allows for spacing and configuration for other components of the leg assembly 26 within the design of the sleeve 90. For example, the locking arm 142 (described in detail below) is coupled to the sleeve 90. In addition, the first bumping surface 80 is positioned on the sleeve 90. Further, the sleeve 90 of the illustrated embodiment is designed with an arch at the knuckle joiner 118 of the hinge assembly 46 (see FIG. 9) for strength optimization of the sleeve 90 in addition to providing spacing for mating with other components of the leg assembly 26.

In addition to the lateral spacing of the center point of the first stopping surface 76 from the central axis X of the leg portion 70, the first stopping surface 76 is also vertically spaced a distance d4 from the hinge assembly 46, as seen in FIG. 12. Such configuration reduces the wear of the hinge assembly 46. When the support device 20 is in the first position (FIG. 12), such that the first stopping surface 76 of the movable portion 48 of the leg assembly 26 mates with the second stopping surface 78 disposed on the chest plate 22, the load of the movable portion 48 of the leg assembly 26 is primarily on the first stopping surface 76, and not on the hinge pin 108 of the hinge assembly 46.

Such vertically and lateral spacing of the first stopping surface 76 from the hinge assembly 46 also allows for complete disengagement of the first stopping surface 76 of the movable portion 48 of the leg assembly 26 and with the second stopping surface 78 of the chest plate 22 when the support device 20 is in the second position (FIG. 13).

Figure 3:
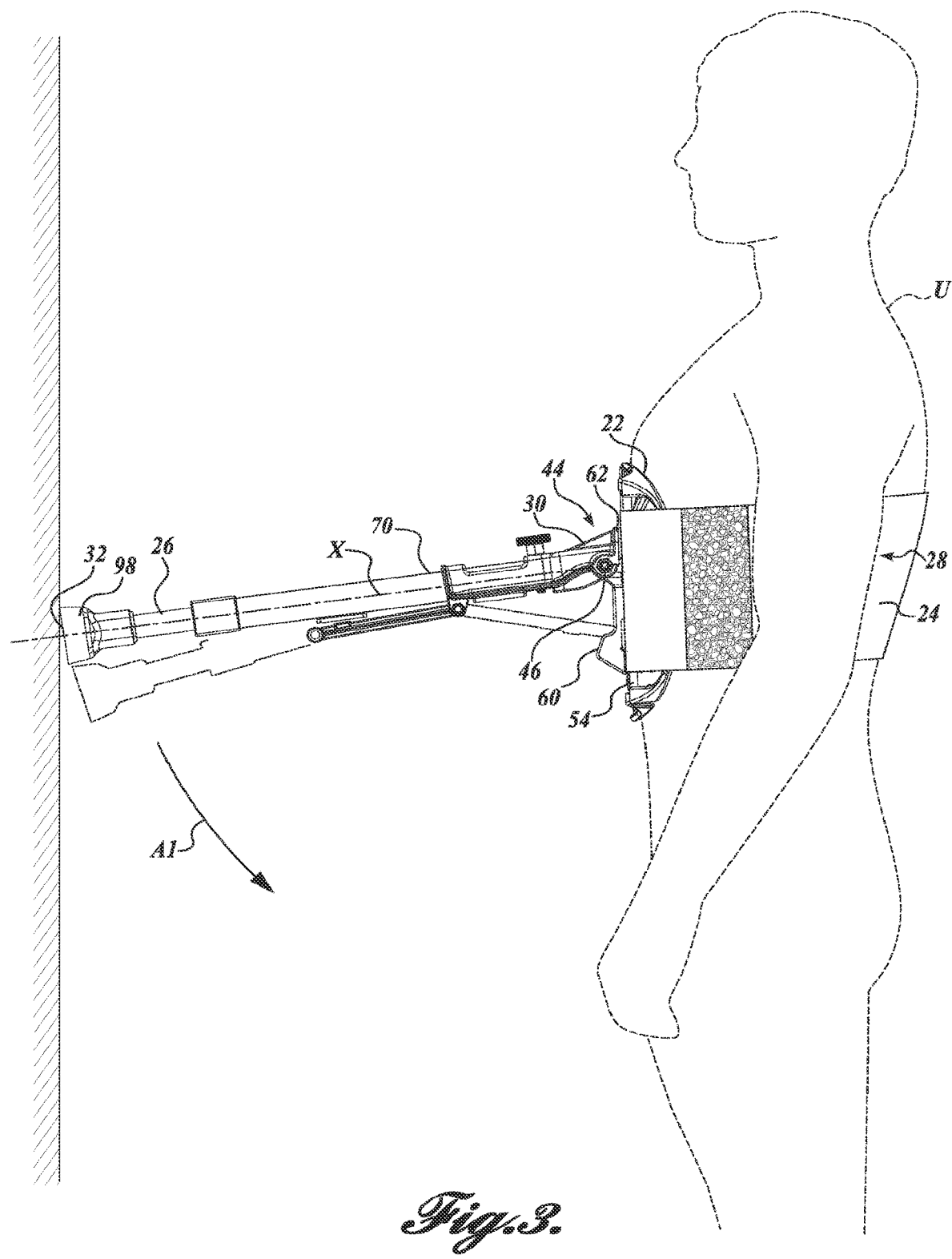
FIG. 3 depicts a side view of the user and the support device of FIG. 1, with the leg portion of the support device in an extended position and in an unlocked configuration.
Figure 4:
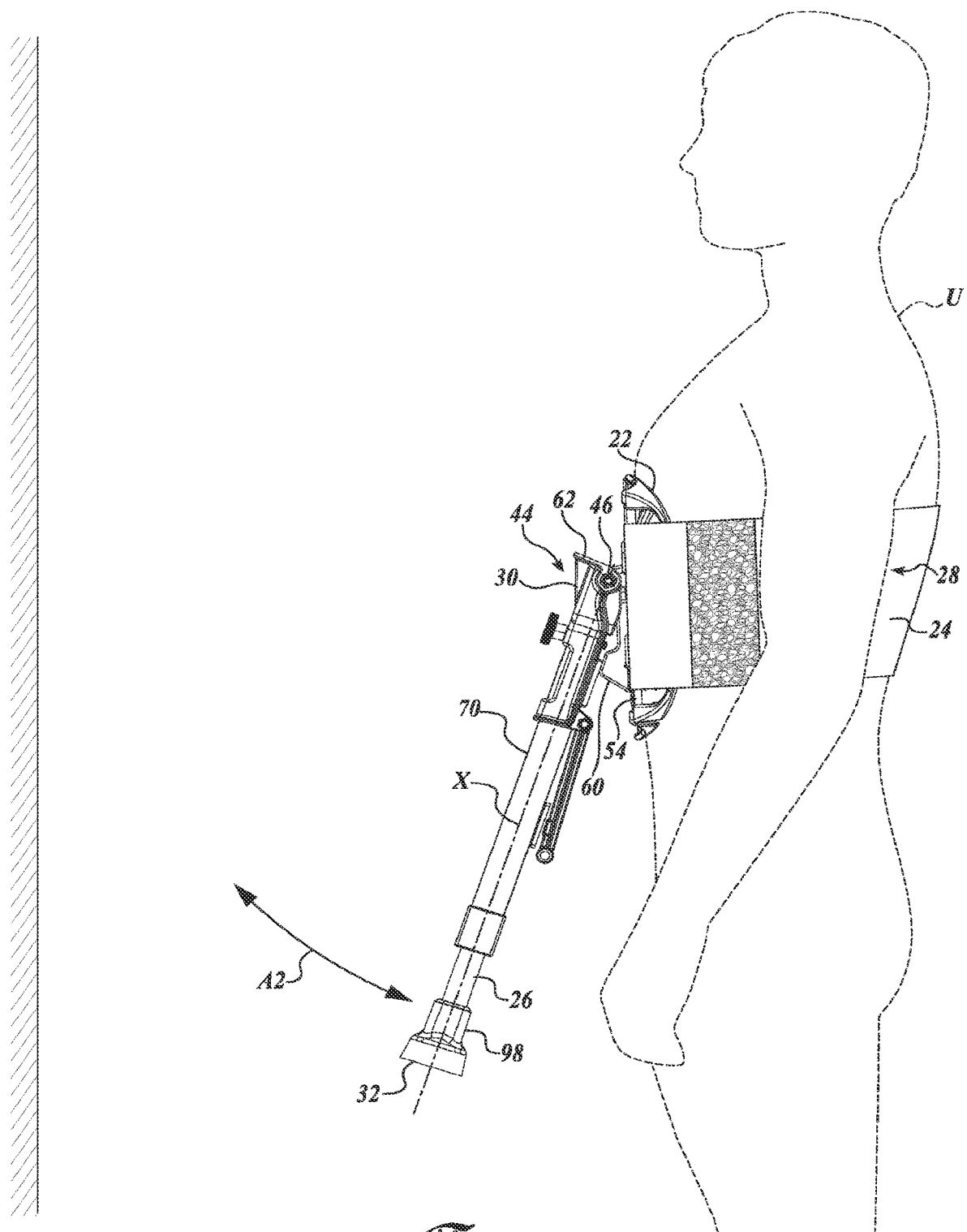
FIG. 4 depicts a side view of the user and the support device of FIG. 1, with the leg portion of the support device in a retracted position.

In the illustrated embodiment, the moveable portion 48 of the leg assembly 26 is configured to contact the stop 62 on the chest plate 22 to prevent the moveable portion 48 of the leg assembly 26 from rotating higher than the pivot range. For example, when the moveable portion 48 of the leg assembly 26 is substantially perpendicular to the chest plate 22 (as shown in FIG. 3), the proximal end 30 encounters the stop 62 to prevent the leg 26 from rotating any further. Preventing the leg 26 from rotating beyond the horizontal position shown in FIG. 3 can help ensure that the moveable portion 48 of the leg assembly 26 does not contact the upper body of the user U, thus avoiding injury to the upper body of the user U.

In the hands and knees position of FIG. 5, the stop also helps to prevent the user from falling face-first over the top of the leg portion 70. In some embodiments, the first and second surfaces 76 and 78 of the stop 62 are formed from rigid materials, such as metal or hard plastic materials. In other embodiments, the first and second surfaces 76 and 78 of the stop 62 may have some elasticity to absorb energy.

The bumper 60 is configured to prevent the leg 26 from rotating outside of the pivot range. In the illustrated configuration of FIG. 4, the contact between the first and second bumping surfaces 80 and 82 of, respectively, the leg assembly and the bumper 60 defines the lowest point at which the leg assembly 26 can rotate. In one embodiment, when the user U is standing vertically (see FIG. 4), the bumper 60 can prevent the leg assembly 26 from rotating down until the leg portion 70 is vertical. Preventing the leg portion 70 from rotating down to vertical can help ensure that the leg portion 70 does not contact the lower body of the user U, thus avoiding injury to the lower body of the user U.

The bumper 60 can also provide the ability for the user U to quickly push out (or "shoot") the leg portion 70. From the position depicted in FIG. 5, the user U may move to push the leg portion 70 from the chest plate 22 quickly. The interaction of the bumper 60 and the moveable portion 48 of the leg assembly 26 causes the moveable portion 48 of the leg assembly 26 to quickly shoot out. As the moveable portion 48 of the leg assembly 26 shoots out, the user U may move his or her body from a first position or a first working location to a second position or second working location when the distal end 32 or the foot 98 touches a surface (e.g., a wall or the ground) at the new desired position.

The ability to shoot the moveable portion 48 of the leg assembly 26 adds to the safety of the support device 20 because the user U can quickly set the moveable portion 48 of the leg assembly 26 if necessary. Also, the ability to shoot the moveable portion 48 of the leg assembly 26 adds to the convenience of the support device 20 because it reduces the amount of time to set up the support device 20 with respect to the user's body.

In some embodiments, the first and second bumping surfaces 80 and 82 are configured from a rigid material (e.g., a metal material or a hard plastic material) or a semi-rigid material (e.g., an elastomeric material). In some embodiments, the user is able to feel the point at which the moveable portion 48 of the leg assembly 26 hits the second bumping surface 82, and the bumper 60 acts as a predictable governor for the user. In some embodiments, when the user is working horizontally, the bumper 60 provides a resistance point that helps a user prevent the user's face from hitting the ground.

As described above, the leg assembly 26 may be releasably coupled to the chest plate 22. The interface for releasable coupling of the leg assembly 26 will now be described with reference to FIGS. 9 and 10. In the illustrated embodiment, the leg assembly 26 includes a leg attachment portion 74 for attaching the leg assembly 26 to a receiving portion 58 on the chest plate 22 such that the leg assembly 26 can pivot relative to the chest plate 22. The attachment portion 74 includes a first attachment section 112, a second attachment section 114, and a third attachment section 116 between the first and second attachment sections 112 and 114.

The first attachment section 112 includes first and second protrusions 120 and 122, which are configured to be received within the first and second receiving sections 124 and 126 of the chest plate 22. The first and second protrusions 120 and 122 are low profile tabs that are configured to be slidingly received within the first and second receiving sections 124 and 126 having a similar profile.

An extension section 128 extends between the first and second receiving sections 124 and 126 on the chest plate 22, shown as a ridge. Likewise, an extension section 138 extends on the leg attachment portion 74 between the first and second protrusions 120 and 122 of the first attachment section 112 (see FIG. 11). The first and second receiving sections 124 and 126 and the extension section 128 therebetween define the second stopping surface 78, configured for interaction with the first stopping surface 76 of the leg assembly 26 (see FIGS. 12 and 13). Extension section 138 on the leg attachment portion 74 may also form a part of the second stopping surface 78.

In one embodiment of the present disclosure, the first and second receiving sections 124 and 126 and the extension section 128 extending therebetween define at least three points of contact between the second stopping surface 78 and the first stopping surface 76 of the leg assembly 26. At least three points of contact provide a stable stop for the user. In addition, ribs or flares 176 along with chest plate 22 tie the first and second receiving sections 124 and 126 and the extension section 128 to the outer circumference of the chest plate 22 adding load distribution to the contact surfaces of the stop system 62.

The second attachment section 114 includes third and fourth protrusions 130 and 132, which (like first and second protrusions 120 and 122) are configured to be received within the third and fourth receiving sections 134 and 136 of the chest plate 22. Like the first and second protrusions 120 and 122, the third and fourth protrusions 130 and 132 are low profile tabs that are configured to be slidingly received within the third and fourth receiving sections 134 and 136 having a similar profile.

The configuration of the first and second spaced attachment sections 112 and 114 on the chest plate 20 allow for load distribution on the chest plate 20 when the support device 20 is in use, while providing a quick release distance of the protrusions from the respective receiving portions.

Although shown as including four protrusions and four receiving portions in the illustrated embodiment, other sliding configurations are within the scope of the present disclosure. For example, each side may include a single elongated protruding section and a single elongated receiving portion for slidingly receiving the protruding section. The configuration of the illustrated embodiment provides for a shorter release motion than elongated protrusions and receiving portions without compromising the stability of the attachment between the leg assembly and the chest plate. In one embodiment of the present disclosure, the release distance may be less than ½ of the length of the leg attachment portion 74. In another embodiment, the release distance may be less than ⅓ of the leg attachment portion 74.

As seen in FIG. 10, the spacing of the receiving sections is different from the first and second receiving sections 124 and 126 and the third and fourth receiving sections 134 and 136. In the illustrated embodiment, the spacing between the third and fourth receiving sections 134 and 136 is closer together than the spacing between the first and second receiving sections 124 and 126 (compare d1 with d2). Such spacing configuration is designed for load distribution and ease of use. In other embodiments of the present disclosure, the spacing may be the same or different in other ways.

The third section 116 of the attachment portion 74 extends between and joins the first attachment section 112 and the second attachment section 114. In the illustrated embodiment, the third attachment section 116 is integrated with the first hinging portion 102 of the hinge assembly 42 for coupling with the second hinging portion 104 of the hinge assembly 46 on the sleeve 90 of the leg assembly 26.

The third section 116 of the attachment portion 74 further includes an arm receiving portion 140 for receiving a locking arm 142, described in greater detail below.

In addition, the third section 116 of the attachment portion 74 defines a recess 144 between the third and fourth protrusions 130 and 132 of the second section 114 of the attachment portion 74. The recess 144 is designed and configured for receiving the latch tab 146 on the chest plate 22 when the leg assembly 26 is coupled to the chest plate 22 (see FIG. 9).

To attach the leg assembly 26 to the chest plate 22, the leg attachment portion 74 of the leg assembly 26 is aligned with the leg receiving portion 58 of the chest plate 22. As the leg assembly 26 is slidingly engaged with the chest plate 22, a latch tab 146 is depressed. When fully engaged, the latch tab 146 is received within the recess 144 of the leg assembly 26 and prevents release without user activation. In the illustrated embodiment, the latch tab 146 is oriented upward when the user is in a standing position (see FIG. 4). Such orientation of the latch tab 146 provide support to the leg attachment portion 74 when subjected to gravitational pull when the user is in the standing position.

To release the leg assembly 26 from the chest plate 22, the latch tab 146 is depressed in the recess 144 by the finger of the user and the leg attachment portion 74 of the leg assembly 26 is slidingly detached from the receiving portion 58 on the chest plate 22.

The recess 144 is designed with nubs or protrusions 148 to help prevent pinching of the fingertip of the user upon release of the leg assembly 26 from the chest plate 22.

Between the first hinging portion 102 on the third section 116 and the arm receiving portion 140 for receiving the locking arm 142, the profile of the third section 116 of the attachment portion 74 is reduced to allow space for other components of the pivoting leg without interferences, such as rear reinforcement 192 for the knuckle joiner and fastener 92 (see the interface of the third section 116 of the attachment portion 74 with the moveable portion 48 of the leg assembly 26 in FIG. 13).

In the illustrated embodiment, the hinge assembly 46 provides for hinged movement between the leg receiving portion 72 of the leg assembly 26 and the attachment portion 74 of the leg assembly 26. When the attachment portion 74 is attached to the chest plate 22, the hinge assembly 46 provides for hinged movement between the leg portion 70 and the chest plate 22. In another embodiment of the present disclosure, the hinge may be directly coupled to the chest plate, thereby providing for hinged movement between the leg portion and the chest plate.

One advantageous effect of decoupling the leg assembly 26 from the chest plate 22 is that the user U can remove the leg assembly 26 from the chest plate 22 without having to remove the entire support device 20 from the user's body. For example, the user U may use the support device 20 at a first work location, detach the leg assembly 26 to move to a second work location to use the support device 20. It may be desirable to move from one work location to another without the leg assembly 26 attached to the user's chest. However, it may also be desirable not to remove the chest plate 22 from the user's chest merely to move from one location to another. In such a case, the user may remove the leg assembly 26 from the chest plate 22 at the first location, move to the second location with the chest plate 22 still attached to the user's chest, and then couple the leg assembly 26 to the chest plate 22 at the second location.

Another example of a benefit of a leg assembly 26 that decouples from the chest plate 22 is that multiple different legs may be used with the same chest plate 22. For example, the user may prefer a particular characteristic of the leg 26 when performing one type of work (e.g., finishing concrete) and a different characteristic of the leg assembly 26 when performing another type of work (e.g., laying tile). A characteristic of the leg assembly 26 can be one or more of a specific length of the leg assembly 26, a particular foot 54 on the distal end 32 of the leg assembly 26, a particular pivot range of the foot 54 with respect to the leg assembly 26, and so forth.

The user may have a different leg for different types of work that the user performs and use the different legs with the same chest plate 22 interchangeably. Thus, the user can use the same chest plate 22 and couple different legs to the chest plate 22 depending on the type of work that the user will be performing. A user can couple one leg assembly 26 to the chest plate 22 to perform one task, decouple that leg assembly 26 from the chest plate 22, and couple another leg assembly 26 to the chest plate 22 to perform another task. The ability to continue wearing the same chest plate 22 when switching legs and/or types of work can save time and add to the overall convenience of the support device 20 to the user.

Referring to FIGS. 15-18, the chest plate 22 support device 20 includes a locking arm 142 configured to prevent pivoting movement of the movable portion 48 of the leg assembly 26 relative to the chest plate 22. The locking arm 142 includes an arm portion 166 and a first end 154 and a second end 156. The first end 154 is pivotably coupled to the movable portion 48 of the leg assembly 26 (for example, coupled to sleeve portion 90 of the leg assembly 26) to move the locking arm 142 between first (locked, see FIG. 15) and second (unlocked, see FIG. 18) positions.

The second end 156 includes a head 158 (see FIG. 11) for engaging with the arm receiving portion 140 on the third section 116 of the attachment portion 74. In the illustrated embodiment, the head 158 laterally extends in first and second directions from the arm portion 166 of the locking arm 142 (see FIG. 11).

When in an unlocked configuration (for example, see FIG. 18), the locking arm 142 can be attached to the movable portion 58 of the leg assembly 26. As can be seen in the exploded view of FIG. 11, first and second components 150 and 152 capable of magnetic attraction are coupled to the locking arm 142 and the leg assembly 26, respectively. When the first and second magnetic components 150 and 152 are engaged, the locking arm 142 is held in its second (unlocked) position (see also FIGS. 11-13).

When locked, the locking arm 142 provides lateral stability to the movable portion 58 of the leg assembly 26 when coupled to the chest plate 22 to prevent movement and/or rotation of the movable portion 58 of the leg assembly 26.

Figure 15:
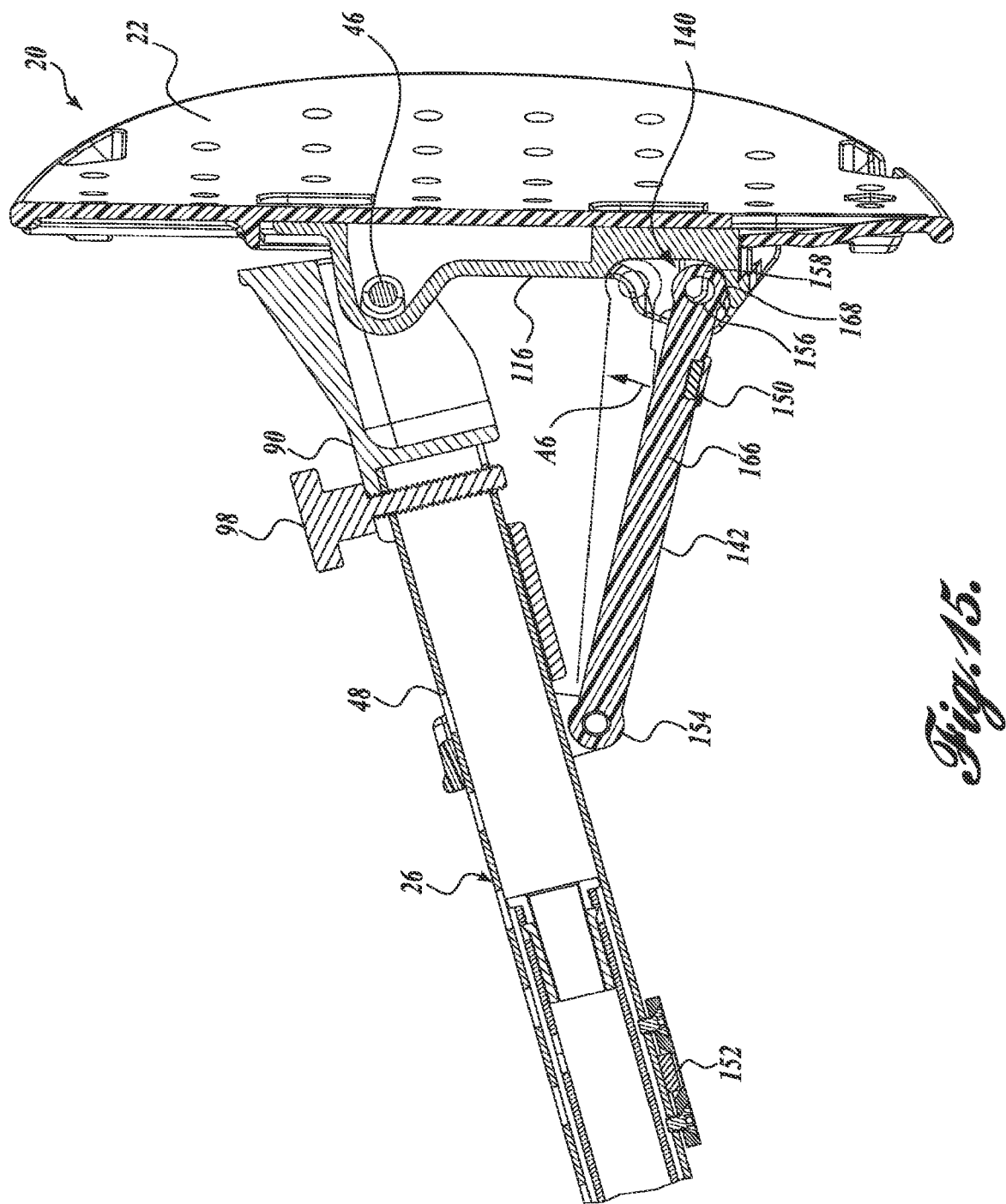

Movement of the locking arm from its first (locked) position, as seen in FIG. 15, to its second (unlocked) position, as seen in FIG. 18, will now be described. When locked, the head 158 of the locking arm 142 nests within the arm receiving portion 140 on the third section 116 of the attachment portion 74. The arm receiving portion 140 includes a contoured cavity 168 designed to receive and mate with the head 158 and first and second lip sections 160 and 162 (see FIG. 11) surrounding a receiver channel 164. When engaged, the lateral extensions from the head 158 are contained within the front portion of cavity 168 by the first and second lip sections 160 and 162. The arm portion 166 of the locking arm 142 extends through the receiver channel 164.

As indicated by arrow A6 in FIG. 15, to remove the locking arm 142 from the arm receiving portion 140, the locking arm 142 is rotated such that the head 158 is positioned in the rear portion of the cavity 168.

Referring now to FIG. 16, with the locking arm 142 is rotated such that the head 158 is positioned in the rear portion of the cavity 168, the movable portion 58 of the leg assembly 26 can be rotated toward the stop 62 as indicated by arrow A7. After such rotation of the leg assembly 26, the head 158 of the locking arm 142 can be rotated over the first and second lip sections 160 and 162 of the arm receiving portion 140, as indicated by arrow A8.

Referring now to FIG. 17, the locking arm 142 can be rotated to its second (unlocked) position, as indicated by arrow A9. When in its second (unlocked) position, the locking arm can be held in place by first and second components 150 and 152 capable of magnetic attraction. Referring now to FIG. 18, when the locking arm 142 is in its second (unlocked position), the movable portion 48 of the leg assembly 26 is free to rotate about its hinge assembly 46 and pivot axis.

To reengage the locking arm 142 in the arm receiving portion 140, the reverse steps are performed. The support device 20 is moved into its extended position (as seen in FIG. 13) with the first and second stopping surfaces 76 and 78 of the stop 62 engaged (see FIG. 17). When the support device 20 is in the extended position, the locking arm 142 can rotate past the arm receiving portion 140 from its first (locked position) to its second (unlocked) position (see FIG. 16). After the locking arm 142 is rotating past the arm receiving portion 140, the head 158 of the locking arm 142 can be nested in the cavity 168 of the arm receiving portion 140 with the arm portion 166 of the lock received in the channel 164 of the arm receiving portion 140 and the head 158 contained by the first and second lips 160 and 162 of the arm receiving portion 140 (see FIG. 15).

When the support device 20 is in its locked configuration and being worn by a user (see FIG. 2), the support device 20 can be used in a standing position or in a hands and knees position (similar to the user position in FIG. 5). When in a hands and knees position, the user is able to reach forward and upward at an angle to work while still being supported by the support device.

In the illustrated embodiment, the locking device 142 is configured for locking in one stabilization angle, for example in a range of 85 to 89 degrees from a vertical axis of the user's body. In other embodiments, a lock system may include multiple stabilization angles, as described in U.S. Pat. No. 10,001,246, the disclosure of which is incorporated herein in its entirety.

Other embodiments of angle stabilization mechanisms, beyond the locking arm 142 depicted in FIGS. 15-18, can be used to limit or prevent pivoting of the movable portion 58 of the leg assembly 26 with respect to the chest plate 22.

In some embodiments, the support device 20 also includes a foot 98 attached to the distal end 32 of the leg portion 70. The foot 98 can be configured from a semi-rigid material, such as rubber, that protects the distal end 32 of the leg portion 70 and resists movement of the distal end 32 of the leg portion 70 against a surface (e.g., a wall or the ground).

In some embodiments, the foot 98 may be larger than the distal end 32 of the leg portion 70. Such an embodiment can distribute the force exerted by the user's weight over a large area and protect both the leg assembly 26 and the surface against which the foot 98 is in contact. In another embodiment that is not depicted, the foot 98 is similar in size to the distal end 32 of the leg assembly 26. For example, the foot 98 can be similar in size to the foot of a crutch or cane.

In the illustrated embodiment, the foot 98 is fixed to the leg assembly 26 such that any pivoting action of the leg assembly 26 will cause a corresponding rotation of the foot 98. In other embodiments, the foot 98 may be configured to move relative to the leg assembly 26.

FIG. 14 depicts an embodiment of a leg carrying device 100 that can be used to carry the leg assembly 26 when it is removed from the chest plate 22. The leg carrying device 100 is configured to receive a knob from knob fastener 98 located on the leg assembly 26. The knob can be inserted through a channel in the leg carrying device 100. The leg carrying device 100 permits the leg assembly 26 to rotate about the knob. Such rotation provides a natural movement of the leg assembly 26 when the user is performing certain activities, such as walking or kneeling down from a standing position.

While illustrative embodiments have been illustrated and described, it will be appreciated that various changes can be made therein without departing from the spirit and scope of the claimed subject matter.

The detailed description set forth herein in connection with the drawings is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The invention claimed is:

1. A body support device, comprising:
    a body attachment portion configured for coupling the body support device to a user, the body attachment portion including a first side and a second side;
    a coupling interface coupled to the first side of the body attachment portion, the coupling interface including a first hinge portion; and
    a leg assembly coupled to the coupling interface, the leg assembly having an elongated member including a first end and a second end, wherein the leg assembly includes a second hinge portion couplable to the first hinge portion to form a hinge assembly for pivotal movement of the elongated member relative to the body attachment portion such that the elongated member is configured for movement between extended and retracted positions, wherein the hinge assembly has a first width and the elongated member has a second width, the first width being wider than the second width.

2. The body support device of claim 1, wherein the body attachment portion includes a rib formed on the first side of the body attachment portion, and wherein the rib is adjacent the first hinge portion.

3. The body support device of claim 2, wherein the rib extends from a central region of the body attachment portion to an outer corner of the body attachment portion.

4. The body support device of claim 1, wherein the leg assembly further comprises a locking arm disposed between the first and second ends of the elongated member, wherein the locking arm is configured to be removably coupled to the coupling interface, and wherein coupling the locking arm to the coupling interface locks the elongated member in the extended position.

5. The body support device of claim 1, wherein the coupling interface includes a first protrusion at a first end of the coupling interface and a second protrusion at a second end of the coupling interface, and wherein the first hinge portion is disposed between the first and second protrusions.

6. The body support device of claim 1, wherein the first hinge portion couples to the second hinge portion by receiving a pin that extends through the first and second hinge portions.

7. The body support device of claim 1, wherein the pivotal movement of the leg assembly is restricted to a pivot range between 0 degrees and 90 degrees in a single plane perpendicular to the body attachment portion or a pivot range between 5 degrees and 85 degrees in a single plane perpendicular to the body attachment portion.

8. A body support device, comprising:
a body attachment portion configured for coupling the body support device to a user, the body attachment portion including a first side and a second side;
a coupling interface coupled to the first side of the body attachment portion, the coupling interface including a first knuckle; and
a leg assembly coupled to the coupling interface, the leg assembly having an elongated member including a first end and a second end, wherein the leg assembly includes second and third knuckles disposed at or adjacent the first end of the elongated member, wherein the second and third knuckles are configured to couple to the first knuckle to form a hinge for pivotal movement of the elongated member relative to the body attachment portion such that the elongated member is configured for movement between extended and retracted positions, wherein the hinge has a first width and the elongated member has a second width, the first width being wider than the second width.

9. The body support device of claim 8, wherein the body attachment portion includes a rib formed on the first side of the body attachment portion, and wherein the rib is adjacent the leg assembly.

10. The body support device of claim 9, wherein the rib extends from a central region of the body attachment portion to an outer corner of the body attachment portion.

11. The body support device of claim 8, wherein the leg assembly further comprises a locking arm disposed between the first and second ends of the elongated member, wherein the locking arm is configured to be removably coupled to the coupling interface, and wherein coupling the locking arm to the coupling interface locks the elongated member in the extended position.

12. The body support device of claim 8, wherein the coupling interface includes a first protrusion at a first end of the coupling interface and a second protrusion at a second end of the coupling interface, and wherein the first knuckle is disposed between the first and second protrusions.

13. The body support device of claim 8, wherein the pivotal movement of the elongated member is restricted to a pivot range between 0 degrees and 90 degrees in a single plane perpendicular to the body attachment portion or a pivot range between 5 degrees and 85 degrees in a single plane perpendicular to the body attachment portion.

14. A body support device, comprising:
a body attachment portion configured for coupling the body support device to a user, the body attachment portion including a first side and a second side;
a coupling interface coupled to the first side of the body attachment portion, wherein the coupling interface includes a first knuckle; and
a leg assembly having a first end coupled to the coupling interface and a second free end, the leg assembly including second and third knuckles disposed at or adjacent the first end and a bridge coupling the second knuckle to the third knuckle, wherein the second and third knuckles are configured to couple to the first knuckle to form a hinge assembly for pivotal movement of the leg assembly such that the leg assembly is configured for movement between extended and retracted positions, and wherein the first knuckle is disposed within a space defined by the bridge, the second knuckle, and the third knuckle.

15. The body support device of claim 14, wherein the body attachment portion includes a rib formed on the first side of the body attachment portion, and wherein the rib is adjacent the second or third knuckle of the leg assembly.

16. The body support device of claim 15, wherein the rib extends from a central region of the body attachment portion to an outer corner of the body attachment portion.

17. The body support device of claim 14, wherein the leg assembly further comprises a locking arm disposed between the first and second ends of the leg assembly, wherein the locking arm is configured to be removably coupled to the coupling interface, and wherein coupling the locking arm to the coupling interface locks the leg assembly in the extended position.

18. The body support device of claim 14, wherein the coupling interface includes a first protrusion at a first end of the coupling interface and a second protrusion at a second end of the coupling interface, and wherein the first knuckle is disposed between the first and second protrusions.

19. The body support device of claim 14, wherein the bridge includes a first reinforcing member disposed on a first side of the bridge, wherein the first reinforcing member is configured to provide strength and load distribution to the second or third knuckles.

20. The body support device of claim 19, wherein the bridge includes a second reinforcing member disposed on a second side of the bridge, wherein the second reinforcing member is configured to support the bridge.

* * * * *